US012778789B2

(12) United States Patent
Mugadza

(10) Patent No.: US 12,778,789 B2
(45) Date of Patent: Nov. 3, 2026

(54) COLLAPSIBLE MENSTRUAL CUP AND METHOD FOR ALLEVIATING MENSTRUAL DISCOMFORT

(71) Applicant: SPRXNG LLC, New Haven, CT (US)

(72) Inventor: Phyllis Mugadza, New Haven, CT (US)

(73) Assignee: SPRXNG LLC, New Haven, CT (US)

( * ) Notice: Subject to any disclaimer, the term of this patent is extended or adjusted under 35 U.S.C. 154(b) by 329 days.

(21) Appl. No.: 18/557,005

(22) PCT Filed: Apr. 28, 2022

(86) PCT No.: PCT/US2022/026712
§ 371 (c)(1),
(2) Date: Oct. 24, 2023

(87) PCT Pub. No.: WO2022/232381
PCT Pub. Date: Nov. 3, 2022

(65) Prior Publication Data

US 2024/0207085 A1 Jun. 27, 2024

Related U.S. Application Data

(60) Provisional application No. 63/181,124, filed on Apr. 28, 2021.

(51) Int. Cl.
*A61F 5/455* (2006.01)
*A61F 5/44* (2006.01)

(52) U.S. Cl.
CPC .......... *A61F 5/4553* (2013.01); *A61F 5/4405* (2013.01)

(58) Field of Classification Search
CPC .. A61F 5/4404; A61F 5/4553; A61F 13/2045; A61F 5/455
See application file for complete search history.

(56) References Cited

U.S. PATENT DOCUMENTS 1,743,733 A * 1/1930 Spardel ................ A61F 5/4553 604/331
2,182,702 A * 12/1939 Previn .................. A61F 5/4553 604/331
3,841,333 A * 10/1974 Zalucki ................ A61F 5/4553 604/330
4,270,539 A * 6/1981 Frosch .................... A61F 5/455 604/347
4,381,771 A * 5/1983 Gabbay ..................... A61F 6/08 128/836
4,846,816 A * 7/1989 Manfredi ............. A61F 5/4405 604/323

(Continued)

FOREIGN PATENT DOCUMENTS

CN 110711068 A 1/2020
CN 112168462 A 1/2021

*Primary Examiner* — Adam Marcetich
*Assistant Examiner* — Ted Yang
(74) *Attorney, Agent, or Firm* — Wiggin and Dana LLP

(57) ABSTRACT

A drainable menstrual cup is described. The menstrual cup has a collapsible and foldable receptacle portion with a rim having a plurality of creases and a collapsible hollow telescoping stem terminating in an optional means for applying suction to generate, create, or apply a negative atmospheric pressure. The cup can also contain a means for draining collected menstrual fluid and can be used for alleviating menstrual discomfort, including pain.

13 Claims, 28 Drawing Sheets

(56) References Cited

U.S. PATENT DOCUMENTS 4,867,177 A * 9/1989 Urheim .................. A61B 46/30 128/849
4,955,875 A * 9/1990 Knowles ............... A61F 5/4553 604/331
5,295,984 A * 3/1994 Contente ............... A61F 5/4553 604/327
5,827,248 A * 10/1998 Crawford .............. A61F 5/4553 604/328
6,168,609 B1 * 1/2001 Kamen ................. A61F 5/4553 600/573
6,559,352 B2 * 5/2003 Zadini .............. A61B 17/12136 604/330
11,291,535 B2 * 4/2022 Conti ................. A61B 10/0045
2001/0018577 A1 * 8/2001 Fitzpatrick ............ A61F 5/4553 604/328
2006/0271019 A1 * 11/2006 Stoller .............. A61M 25/0017 604/353
2007/0225688 A1 * 9/2007 Goodwin .......... A61M 25/0017 604/327
2008/0077097 A1 3/2008 Chambers et al.
2008/0300448 A1 * 12/2008 Frazier .................... A61F 5/455 600/29
2014/0276494 A1 * 9/2014 Cisko .................... A61M 1/602 604/327
2015/0000024 A1 * 1/2015 Plath ..................... A61F 5/4404 4/301
2017/0189222 A1 * 7/2017 Lin ....................... A61F 5/4553
2018/0311069 A1 * 11/2018 Hjorth ................... A61F 5/4553
2019/0021898 A1 * 1/2019 Ahn ...................... A61F 5/4553
2019/0192335 A1 6/2019 Sedic
2019/0262167 A1 * 8/2019 Guidry .................... A61F 5/445
2020/0022835 A1 * 1/2020 Lloveras Macià .... A61F 5/4404
2020/0046572 A1 * 2/2020 Hwang ................. A61F 5/4404
2020/0060865 A1 * 2/2020 Hwang ................. A61F 5/4553
2020/0078208 A1 3/2020 Stoebe-Latham
2020/0138620 A1 * 5/2020 Schwab .................. A61F 5/453
2020/0206019 A1 * 7/2020 Brown .................. A61F 5/4553
2020/0330288 A1 * 10/2020 Duensing ................ A61F 13/26
2020/0375788 A1 * 12/2020 Zhang ................... A61F 5/4553
2021/0022770 A1 * 1/2021 Joseph ...................... A61F 6/08
2021/0022912 A1 * 1/2021 Johnson .................. A61F 5/449
2021/0069009 A1 * 3/2021 Im ......................... A61F 5/4553
2021/0128342 A1 * 5/2021 Miller ..................... A61F 5/455
2021/0137725 A1 * 5/2021 Shaviv ................. A61B 5/4337
2021/0251815 A1 * 8/2021 Brown ................ A61F 13/2045
2022/0175575 A1 * 6/2022 Cull .......................... A61F 7/10
2022/0331145 A1 * 10/2022 Goodrich ................ A61F 5/455

* cited by examiner

COLLAPSIBLE MENSTRUAL CUP AND METHOD FOR ALLEVIATING MENSTRUAL DISCOMFORT

CROSS-REFERENCE TO RELATED APPLICATIONS

This application claims the benefit under 35 U.S.C. § 119(e) of U.S. Provisional Application No. 63/181,124, filed Apr. 28, 2021, and is a National Stage (§ 371) Application of International Application No. PCT/US2022/026712, filed Apr. 28, 2022, all of which are herein incorporated by reference in their entirety.

FIELD OF THE INVENTION

The present invention provides a drainable menstrual cup. The menstrual cup has a collapsible and foldable receptacle portion with a pre-creased rim and a collapsible hollow stem having a drainage means, and optionally a means for applying a suction or negative pressure. The stem can be used to insert and position the menstrual cup within the vagina, and also for removal from the vagina. The stem, which is in fluid communication with the receptacle portion, can also be used to extend the cup during insertion. The menstrual cup is also useful for alleviating menstrual discomfort, including pain, and other pelvic discomfort or pain.

BACKGROUND OF THE INVENTION

In the feminine hygiene market, the commonly used products are disposable sanitary pads and tampons. The average user discards an astonishing 125 kg-150 kg of tampons, pads and applicators in a lifetime. Reusable menstrual cups and reusable menstrual discs are an economical and eco-friendly alternatives to disposable menstrual products.

Menstrual cups and menstrual discs are generally known, are used internally, and are intended to be reused. Menstrual cups are tucked behind the pubic bone which holds them in place. In contrast to menstrual cups, menstrual discs are inserted to sit in the vaginal fornix, at the base of the cervix. The choice of which product to use is influenced by the anatomy of the user, such as how high or low the cervix or the uterus is of the user, as well as the tilt of the uterus.

Known menstrual cups and menstrual discs have a number of disadvantages. These products are difficult to insert, particularly for individuals with loss of dexterity or grip strength. Insertion of these products is generally performed by folding the disc or cup using known folding techniques. The product is then inserted into place, where it unfolds and returns to its initial shape. Even when the menstrual cup or disc is folded according to the above methods, there is a limitation in reducing the size of the product for folding and insertion, and many users still experience a feeling of repulsion or experience discomfort during insertion.

Some menstrual cups have a drainage mechanism. These menstrual cups that have included drainage mechanisms do not allow for the device to be drained when it is inside the body because the stems are not designed to extend outside the vagina nor are readily accessible.

For example, US Patent Application publication No. US 2019/0192335 A1, to Sedic, published Jun. 27, 2019, describes a receptacle but this receptacle does not include a stem. Furthermore, the rim does not include a pre-creased design to allow for folding or to reduce the size of the device during insertion.

US Patent Application publication No. US 2008/0077097 A1, to Chambers, published Mar. 27, 2008 and US Patent Application Pub. No.: US 2020/0078208 A1, to Stoebe-Latham, published Mar. 12, 2020 describe traditional menstrual cups. These cups sit in the vaginal canal and therefore, are not designed to be worn during sexual intercourse. These cups include a solid stem that does not permit drainage nor a means of applying varying levels of negative pressure to the receptacle.

If an applicator is used with the menstrual device, users have less control over how far up the product is inserted or exactly where the product is placed. It is important for these products to be placed in a position that is correct for the user's body. Furthermore, for proper functioning without leakage, the product must be completely unfolded when it is positioned for use. Existing menstrual cups often do not completely unfold under their own mechanical spring forces and require a user to reach further into the vagina to inspect the shape, and if necessary, manipulate the cup to complete the unfolding. In the case of menstrual discs, these devices are pinched and folded in half at the rim before they are inserted into the vaginal canal and pushed toward the cervix as far as they can comfortably be inserted. Next, the user tucks the rim behind the pubic bone. If the disc is not held in place and in the correct position, leakage can occur.

Reusable menstrual products generally lack a function to aid in the insertion of the cup or disc. These products also tend to present challenges during their removal. Removal of existing menstrual cups and discs should be accomplished on a regular basis for emptying and cleaning. If removal is inconvenient for the user and not accomplished as often as it should be, this may lead to hygienic problems or blood leakage. Sometimes, the user is embarrassed to clean the menstrual cup or disc at the sink of a public lavatory. These are some of the reasons why these products are not generally as widely accepted and used as they could be.

Some menstrual cups include a solid, gripped stem to aid with the removal of the cup. Existing menstrual discs do not include stems in their design. Removing a menstrual disc is achieved by untucking the product from the pubic bone. However, this can cause the disc to tip sideways and for spillages to occur. Furthermore, it is difficult to determine the amount of fluid collected in the device before the menstrual cup or disc needs to be removed. If a menstrual product can be drained without needing to be removed, it may become more convenient to manage the menstrual product and aid consumer compliance.

Furthermore, the presence of a stem or a silicon string in the vagina can be irritating for some users. The stem prevents users from wearing menstrual cups during sexual intercourse. Menstrual discs can be worn during sexual intercourse due to the absence of a stem in the vaginal canal.

A great challenge that menstruators face independent of the products they use is dysmenorrhea. Dysmenorrhea, commonly known as menstrual or period pains, is the leading cause of recurrent school or work absenteeism among the menstruating population. There are several options for treating menstrual pains, but existing therapies are separate from the menstrual products available today.

A combination of inactivity due to menstrual pain and the time lost due to changing and inserting menstrual products reduces hours of productivity among menstruators. Both menstrual discs and menstrual cups have advantages and disadvantages which force users to make trade-offs when deciding which products to use. Therefore, there is a need for an improved reusable menstrual product which overcomes the disadvantages of the prior art. What is needed, therefore, is a product that does not restrict the vaginal canal and includes mechanisms for insertion, drainage, and menstrual discomfort or pain relief.

The present invention thus provides a menstrual cup for dealing with menstruation and managing menstrual discomfort and pain.

SUMMARY OF THE INVENTION

The present invention provides a drainable and collapsible menstrual cup. The menstrual cup has a collapsible and foldable receptacle and a collapsible hollow telescoping stem. The stem can be used to insert and position the menstrual cup within the vagina and for removal from the vagina. The stem can also be used to extend or deploy the cup during insertion. The stem can also contain a means for draining collected menstrual fluid. The stem can optionally interface with a removable suction bulb for applying negative atmospheric pressure to the interior of the menstrual cup.

In some embodiments, the present disclosure provides for a collapsible menstrual cup, comprising;

(a) a circular, concave receptacle having a rim comprising a plurality of creases, the receptacle being collapsible and foldable along the creases into a folded state and conversely extendable and un-foldable into an unfolded state;

(b) a hollow telescoping stem in fluid communication with the concave receptacle and having a diameter at an end proximal to the concave receptacle dimensioned for accepting the receptacle in its folded state, the hollow telescoping stem being collapsible and conversely extendable; and (c) a discharge valve disposed at an end of the hollow telescoping stem distal to the concave receptacle.

In further embodiments, the device has a concave inner surface (for orientation into the vagina for collection of menstrual fluid) and a convex outer surface.

In further embodiments, the discharge valve forms a portion of or is in fluid communication with a discharge orifice.

In further embodiments, the discharge valve is a duckbill valve.

In further embodiments, the discharge valve is contained at least partially within the distal end of the hollow telescoping stem.

In further embodiments, a portion of the hollow telescoping stem surrounding the discharge valve comprises tactile features aligned with an actuation direction of the discharge valve.

In further embodiments, the action of a user pinching the tactile features together in the actuation direction of the discharge valve opens the valve to discharge fluid, and wherein releasing the pinching allows the valve to close to contain fluid.

In further embodiments, the discharge valve comprises a rim protruding from and surrounding the distal end of the hollow telescoping stem.

In further embodiments, the rim is releasably engageable with an external means for applying a negative atmospheric pressure.

In further embodiments, the means for applying (or creating) a negative atmospheric pressure is a suction bulb.

In further embodiments, the suction bulb is capable of applying a circumferential force to the rim to provide an airtight seal.

In further embodiments, the application of circumferential pressure opens the discharge valve for fluid and air communication from the menstrual cup to the suction bulb.

In further embodiments, the stem is offset from the center position of the receptacle.

In further embodiments, the stem is located at the center position of the receptacle.

In some embodiments, the present disclosure provides for a method for collecting and/or draining menstrual fluid from a female subject using a menstrual cup.

In some embodiments, the present disclosure provides for a method for collecting and/or draining menstrual fluid from a female subject using a menstrual cup.

In some embodiments, the suction bulb is squeezed and released to create a negative atmospheric pressure (suction) to facilitate removal of menstrual fluid.

In some embodiments, the present disclosure provides for a method of alleviating or reducing pressure on the vagina and/or the uterus in a female subject using a menstrual cup.

In some embodiments, the suction bulb is squeezed and released to create a negative atmospheric pressure to relieve pressure on the vagina and/or the uterus.

In some embodiments, the present disclosure provides for a method of relieving menstrual pain or discomfort in a female subject using a menstrual cup.

In some embodiments, the suction bulb is squeezed and released to create a negative atmospheric pressure to relieve pressure on the vagina and/or the uterus.

In some embodiments, the present disclosure provides for a collapsible menstrual cup, comprising;

(a) a circular, concave receptacle having a rim comprising a plurality of creases or folds;

(b) a hollow telescoping stem; and (c) a suction bulb, wherein the stem has a first end attached to the receptacle and a second end attached (permanently or releasably) to the suction bulb, wherein each of the receptacle and stem are collapsible and foldable, and conversely extendable and un-foldable, and wherein the device has a concave inner surface (for orientation into the vagina for collection of menstrual fluid) and a convex outer surface.

In further embodiments, the stem further comprises a drainage means.

In further embodiments, the drainage means is an orifice which further comprises a means for opening and closing the orifice, such as a tab.

In further embodiments, the means for opening and closing the orifice is controllable by a tab.

In further embodiments, the suction bulb is deformable and provides a means to apply negative pressure to the receptacle.

In further embodiments, the stem is offset from the center position of the receptacle.

In further embodiments, the present disclosure provides for a method for collecting and/or draining menstrual fluid from a female subject using a menstrual cup.

In further embodiments, the suction bulb is squeezed and released to create a negative atmospheric pressure to facilitate removal of menstrual fluid and to relieve pressure on the vagina and/or the uterus.

In further embodiments, the present disclosure provides for a method of alleviating or reducing pressure on the vagina and/or the uterus in a female subject using a menstrual cup.

In some embodiments, the suction bulb is squeezed and released to create a negative pressure to facilitate removal of menstrual fluid and to relieve pressure on the vagina and/or the uterus.

In some embodiments, the present disclosure provides for a method of relieving menstrual pain or discomfort in a female subject using a menstrual cup.

In some embodiments, the suction bulb is squeezed and released to create a negative pressure to facilitate removal of menstrual fluid and to relieve pressure on the vagina and/or the uterus.

These and other aspects of the present invention will become apparent from the disclosure herein.

BRIEF DESCRIPTION OF THE DRAWINGS

FIG. 9A (left) is a cross sectional view. FIG. 9B (right) is a view showing the location and orientation (in phantom dotted lines) of the fully folded menstrual cup with respect to the stem of the cup. FIGS. 9A and 9B are for illustration purposes and are not to scale.

In FIG. 11A (left) the inner concave side of the receptacle is seen, whereas in FIG. 11B (right) the outer convex side of the receptacle is seen.

FIG. 12A (left) shows the drainage slot in an open position when the drainage part of the stem is extended. The slot is indicated by the dashed arrow. FIG. 12B (right) shows the drainage part of the stem collapsed. The tab over the closed slot is indicated by the solid arrow. The tab indicates to a user where the drainage slot is located when the drainage part of the stem is collapsed.

DETAILED DESCRIPTION OF THE INVENTION

Figure 1:
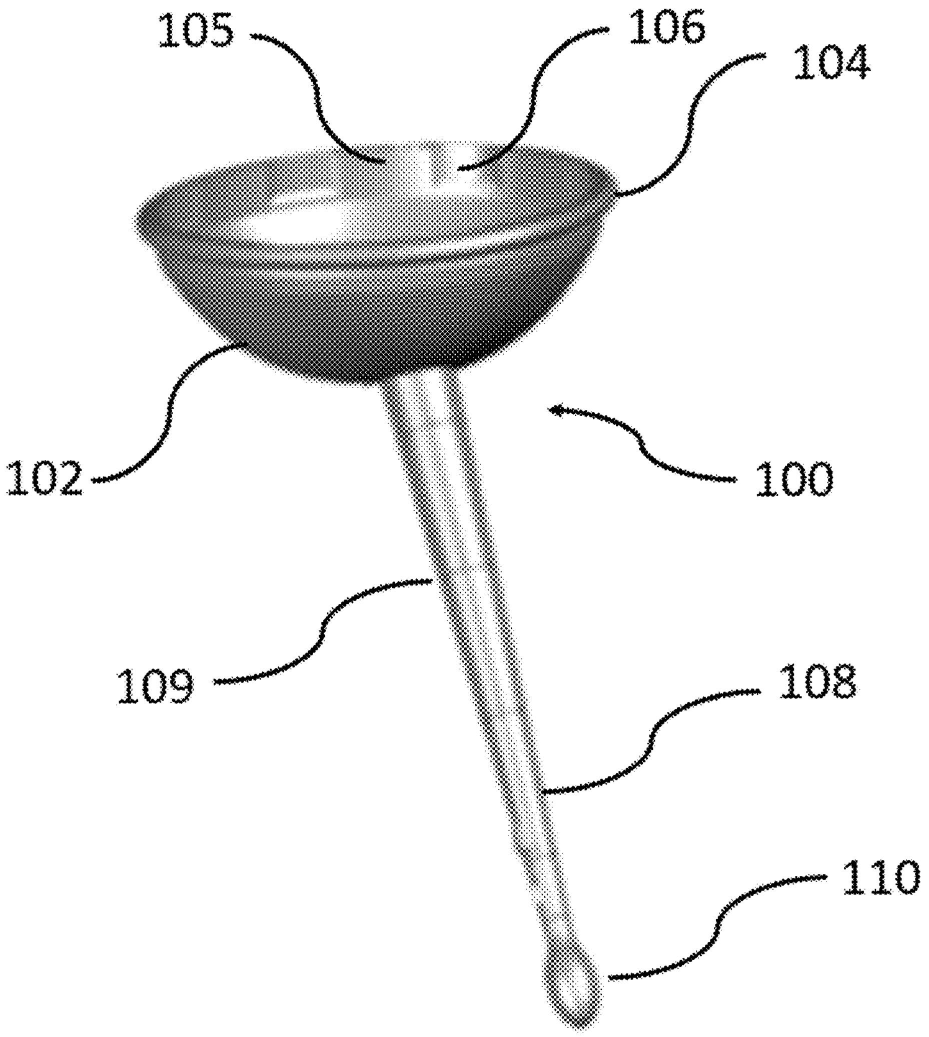
FIG. 1 shows the device with the receptacle open and the stem completely extended. From this orientation, the components of the device are visible: the creased rim, the receptacle, the stem, the drainage system, and the suction bulb.

The present invention provides a drainable menstrual cup. The menstrual cup has a collapsible and foldable receptacle portion with a rim having a plurality of creases and a collapsible hollow telescoping stem. The stem can be used to insert and position the menstrual cup within the vagina, and also for removal from the vagina. The stem can also be used to extend the cup. The stem can contain a means for draining collected menstrual fluid, such as a valve. The menstrual cup is useful for alleviating menstrual pain and other pelvic pain Definitions As used herein, the following terms and abbreviations have the indicated meanings unless expressly stated to the contrary.

The term "alleviating" as used herein means that the menstrual cup can be used to alleviate, reduce the severity of, treat, or prevent menstrual pain and discomfort.

The term "menstrual cup" is used to indicate a menstrual hygiene device that is inserted into the vagina to collect menstrual fluid (blood from the uterine lining). Alternatively, the device can also be described by the term "menstrual disc". However, menstrual discs do not normally have a stem, but rather the disc would refer to the roughly circular portion that is designed to fit into and conform to the vagina for collecting the menstrual fluid. This disc or disc portion can be referred to as a receptacle. Unlike tampons and pads, menstrual cups perform their function by containing fluids, rather than absorbing them. Menstrual cups can be either disposable to be discarded after a single use or reusable for many uses.

Menstrual Cup

The spring energy of the rim causes the receptacle to open. The creases are present on the inside of the rim in an alternating fashion to create the folded state of the device at insertion. The rim is designed with a circular top lip and a flat bottom lip to ensure that it clips into the stem. When the rim is dislodged from this position, the spring energy causes the disc to open. The rim helps to prevent leakage by ensuring that fluid flows into the receptacle and not outside the receptacle.

The term folds, or creases, are meant to be used interchangeably and describe the characteristics of the receptacle such that it can be readily folding at the folds or creases. The fold type is an accordion style fold made up of creases on the inner side of the rim. The folds or creases on the receptacle allow for the receptacle portion of the menstrual cup to be folded, "origami style" to as compact as about $\frac{1}{6}^{th}$ its unfolded size as measured by the diameter, radius, or circumference of the cup or receptacle. In some embodiments, the receptacle is folded to about half (½) of its size. In other embodiments, the receptacle is folded to about one third (⅓) of its size. In other embodiments, the receptacle is folded to about one quarter (¼) of its size. In other embodiments, the receptacle is folded to about one fifth (⅕) of its size. In other embodiments, the receptacle is folded to about one sixth (⅙) of its size. In other embodiments, the receptacle is folded to about one seventh (1/7) of its size. In other embodiments, the receptacle is folded to about one eight (⅛) of its size. In other embodiments, the receptacle is folded to about one ninth (1/9) of its size. In other embodiments, the receptacle is folded to about one tenth (1/10) of its size.

The menstrual cup has a collapsible and foldable receptacle and a collapsible hollow telescoping stem. The menstrual cup is removed out of its case in its rest/starting position. This is when the stem is collapsed to the point where it meets the base of the receptacle that is tucked into the end of the stem proximal to the cup. A user then extends the stem based on how high or low their cervix is. A user then inserts the menstrual cup into the vagina. Once in place, the user then collapses the stem which pushes the receptacle out of the stem. Once the receptacle is completely open and placed in the fornix, the stem can remain fully collapsed and absent from the vaginal canal. If a user wishes to drain the device or induce the suction pressure, the user can extend the stem until it is revealed outside the vagina. The menstrual cup is removed and is placed back into the case.

The device can be cleaned using water and soap. When soapy water is poured into the device, one can shake the device to clean it. The bulb can be squeezed multiple times to clean it. The device is extended and collapsed via the stem to clean the device while soapy water is inside the device. The soapy water and rinse water can be drained through the drainage slot.

During insertion, the stem acts as a built-in applicator with the receptacle tucked into the stem. A user then extends the stem depending on how high or low their cervix is. The device is then inserted into the vagina and once it reaches the fornix, a user can collapse the stem to dislodge and unfold the receptacle.

The telescoping stem can be collapsed or extended which gives the users the option of having the stem absent or present in the vagina. The stem also acts as a channel to create varying degrees of negative pressure induced by a means for applying a negative pressure, such as a suction bulb, based on the extension of the stem when the bulb is squeezed. In some embodiments, the means for applying a negative pressure is a built-in suction bulb located at an end of the stem distal from the cup. In some embodiments, the means for applying a negative pressure is a detachable suction bulb which is releasably detachable from the end of the stem. The suction bulb, whether permanently attached or detachable in various embodiments, is located at the bottom of the stem and is squeezed to induce a negative pressure at the receptacle. The suction is released each time the device is drained to create an intermittent pressure. This control of pressure can be used to help relieve menstrual cramps and other pelvic pain Receptacle Folding and Telescoping Stem Characteristics The ribbing feature on the rim of the receptacle portion of the cup aids in folding during manufacture and also in the folding and opening during use such as during insertion, withdrawal, and when in position.

The telescoping stem is extendable and collapsible. During the insertion process, the stem acts as a built-in applicator to aid in unfolding of the receptacle portion. Initially, for ease of insertion of the device, the stem is extended and the receptacle is folded and tucked into the stem. Once in place, the stem may be collapsed into the receptacle to cause the receptacle portion to unfold.

In various embodiments, the stem has a valve located at or near its end distal to the cup. The purpose of the valve is to discharge collected fluid with the stem in a partially or fully extended state. Such a valve is an example of a drainage means. The valve may take on any shape, characteristics, or mechanism of function so long as the valve is useful for draining the collected fluid. In certain embodiment, the valve is pressure-activated or pinch-activated by the user pinching the walls of the stem to open the valve. In such embodiments, the valve may be intermittently opened by the user to drain the fluid without any additional means of applying a negative pressure. In some embodiments, the valve may be a duckbill valve having an elongated shape at its sealable end which, when pressed along the elongated dimension, is opened. The duckbill valve may be partially or fully contained within the stem and may be actuated by pinching the walls of the stem together. In some embodiments, the stem may have one or more raised, recessed, or other tactile features to indicate to the user where the walls should be pinched to open the valve and to drain the fluid.

In an embodiment, the valve is located at the end of the stem distal from the cup and may have a ridge protruding from the end of the stem which is configured and dimensioned to accept an optional and removable suction bulb. In a state where there is no suction bulb mated to the valve ridge, the valve is in a closed state to retain the fluid. Once the bulb is mated to the valve ridge by pressing the bulb onto the valve ridge, the circumferential pressure applied by the mated region of the bulb may be sufficient to partially or fully open the valve to allow fluid to drain or to allow a negative pressure to be applied to the menstrual cup using the bulb. In alternative embodiments, a suction bulb may be engaged with a straw which may be inserted through the valve to open it for the passage of air and/or fluids collected by the menstrual cup. A "straw" is a hollow structure or tube engageable with a suction bulb at a first end and insertable through a valve at its second end.

Releasably attachable bulbs may comprise one or more holes to allow for repeated squeezing in case a user wishes to apply further negative pressure. Such holes allow for air to enter the bulb in order for it to expand from a compressed state to a filled state. The user may keep the hole plugged with a finger in order to retain the negative pressure for a certain period of time. Once the user's finger is released from the hole, the pressure within the cup will equilibrate with the external pressure, resulting in the bulb expanding to its uncompressed state. In an embodiment, the bulb has one or more tactile features to allow the user to easily locate the hole or to ergonomically actuate the hole using a finger.

In alternative embodiments, releasably attachable bulbs may not have any holes and may be configured for applying multiple squeezes. Particularly, the wall thickness of the bulb may be increased and one or more elasticity-enhancing features, such as a relatively thicker band around the exterior of the bulb, may be added. It can be appreciated that any bulb design for applying a negative pressure to the menstrual cup is contemplated.

In alternative embodiments, extending the telescoping stem will elongate the stem, and when extended fully, expose a drainage slot. A drainage slot is another example of a drainage means. The telescoping stem may also incorporates an anti-spill safety feature whereby an amount of additional force is required to extend the telescoping stem portion that otherwise covers the drainage slot. This feature prevents the user from accidentally discharging fluid from the stem.

Exemplary Embodiments

The menstrual cups of the present disclosure generally have a collapsible and foldable receptacle and a collapsible hollow telescoping stem which is selectably openable via a drainage means to drain collected fluids, and various embodiments are described with certain features that may be incorporated in various permutations of the disclosed menstrual cups. Description of particular embodiments should be taken as non-limiting and a person of skill in the art would recognize that the described features and characteristics describe any scope of embodiments incorporating or omitting any number of such features and characteristics.

FIG. 1 depicts and exemplary embodiment of a menstrual cup 100 having a collapsible and foldable receptacle 102 and a collapsible hollow telescoping step 108. The hollow telescoping stem 108 adjoins the receptacle 102 at a position generally distal from a top rim 104 of the receptacle. The interior of the hollow telescoping stem 108 is in fluid communication with the receptacle 102 such that fluids collected in the receptacle 102 may flow into the stem 108. In some embodiments, the stem 108 is centered at the bottom of the receptacle 102. In some embodiments, the stem 108 is off-center at the bottom of the receptacle 102. The receptacle 102 and stem 108 are generally constructed from the same material and are of unitary construction. In alternative embodiments, the receptacle 102 and stem 108 are separate pieces which are fluidly connected.

The receptacle 102 has a top rim 104 defining a circular profile of the receptacle 102 having a domed shape. In alternative embodiments, the receptacle 102 may take on various shapes so long as it is useful to collect and drain fluid to the stem 108. The rim 104 is generally defined on its inner edge by one or more creases 106 which define regions where the receptacle can be folded. The creases 106 are adjacent to thicker regions 105 which do not have a crease. The creases 106 may be alternatively referred to as folds or depressions, such as depressions 106 in the rim. The regions 105 without creases generally define a thickness of the rim and the creases 106 may be referred to as regions having a thickness less than the thickness of the rim. Alternatively, such regions 106 may be referred to as regions which are relatively thinner than the thickness of the rim.

The creases 106 each define a folding plane of the receptacle 102 such that the domed portion of the receptacle folds along the plane of the crease 106. The folding planes may generally be defined as orthogonal to the circumferential plane of the rim 104. The folding planes being orthogonal to the circumferential plane of the rim is particularly advantageous because the receptacle, when folded, will have a smaller circumference than the receptacle in its unfolded state (see, eg., FIGS. 8 and 16). This smaller circumferential profile is advantageous because insertion into the vagina and placement is easier and the unfolded circumference can be further dimensioned for secure placement and fluid retention once the receptacle is expanded.

The hollow telescoping stem 108 is collapsible along one or more ribs 109 which are approximately parallel to the plane of the rim 104. In embodiments where the stem 108 is off-centered on the receptacle 102 it can be appreciated that the degree to which the ribs 109 are parallel with the rim 104 depends upon the profile of the receptacle and it is generally contemplated that the stem 108 telescopes toward or away from the receptacle 102. Generally, the stem 108 telescopes in a direction orthogonal to the folding planes of the receptacle 102. The orthogonality between the folding plane of the receptacle 102 and the telescoping direction of the stem 108 is particularly advantageous for the "origami style" folding capability of the devices as disclosed herein. These advantages will be described in connection with FIG. 16 in the following description.

Figure 2:
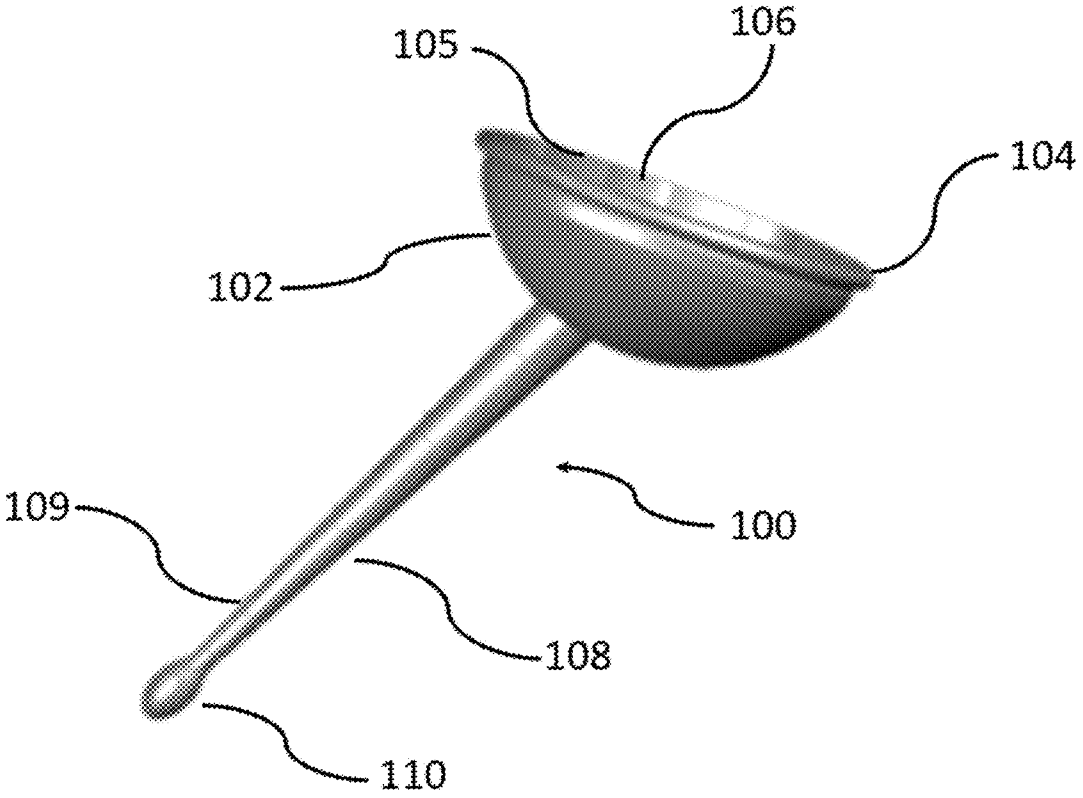
FIG. 2 shows the offset position of the stem with respect to the receptacle.
Figure 3:
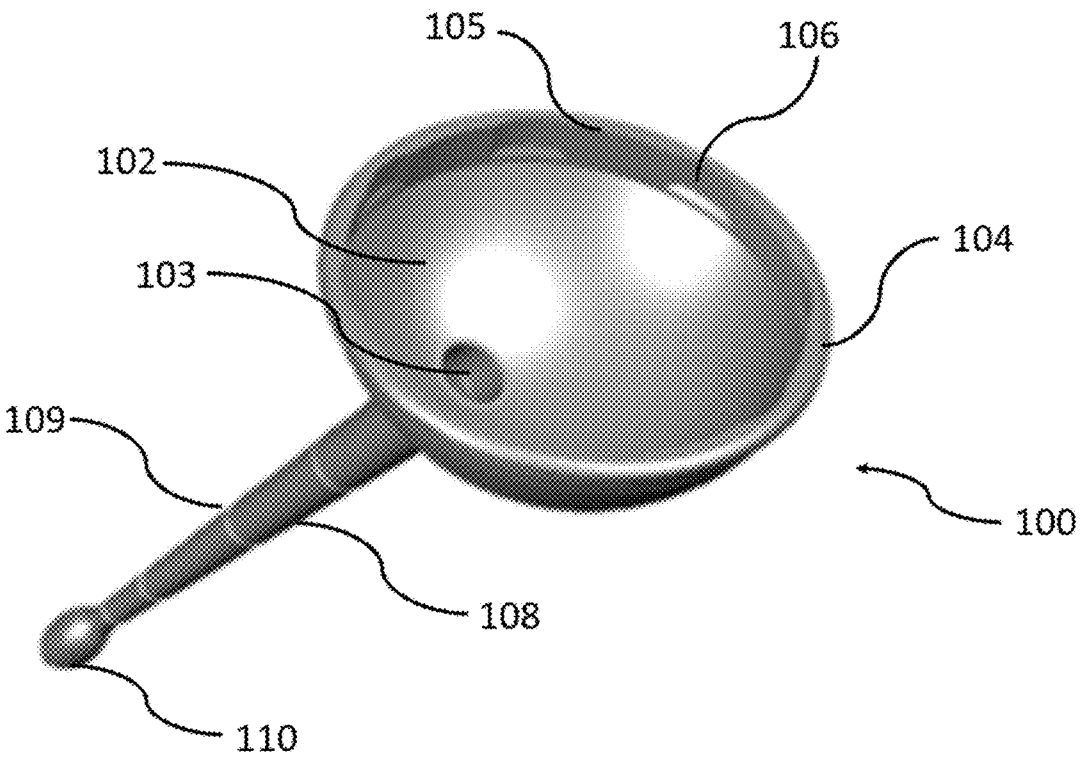
FIG. 3 shows the position at which the hollow stem connects with the receptacle, and demonstrates that fluid can flow from the receptacle and into the hollow stem.
Figure 4:
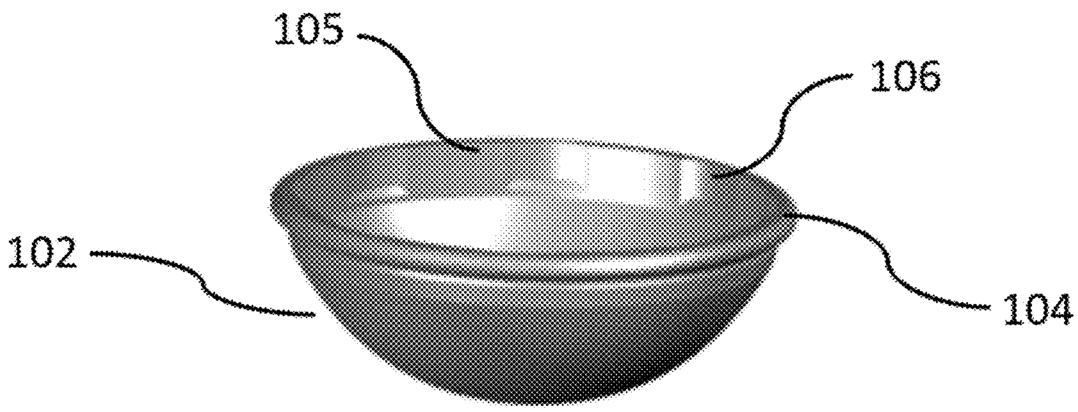
FIG. 4 shows an exemplary receptacle and rim. The rim is separated in half by a groove (notch) that runs around the circumference of the rim. When the receptacle is folded into the stem, the stem clips into a further groove that is located under the rim of the receptacle.
Figure 5:
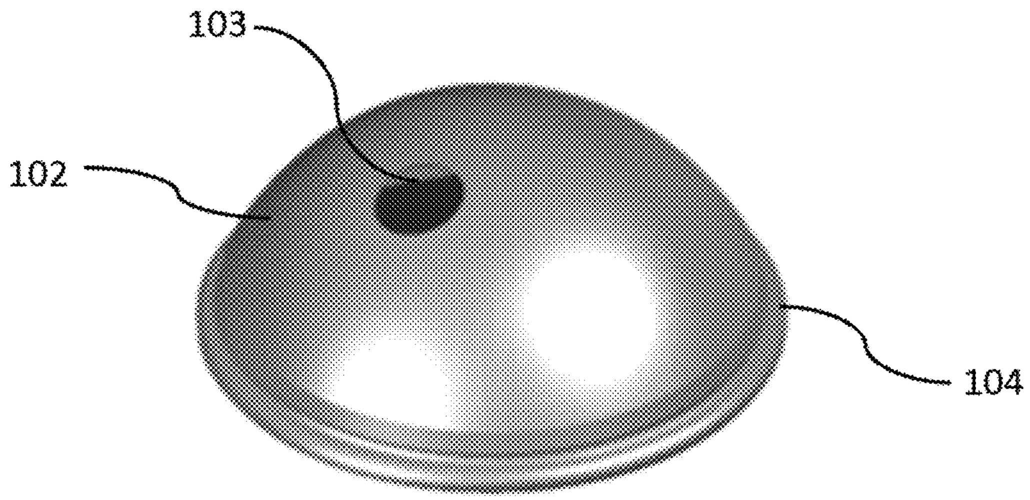
FIG. 5 shows the position at which the hollow stem connects with the receptacle.
Figure 14:
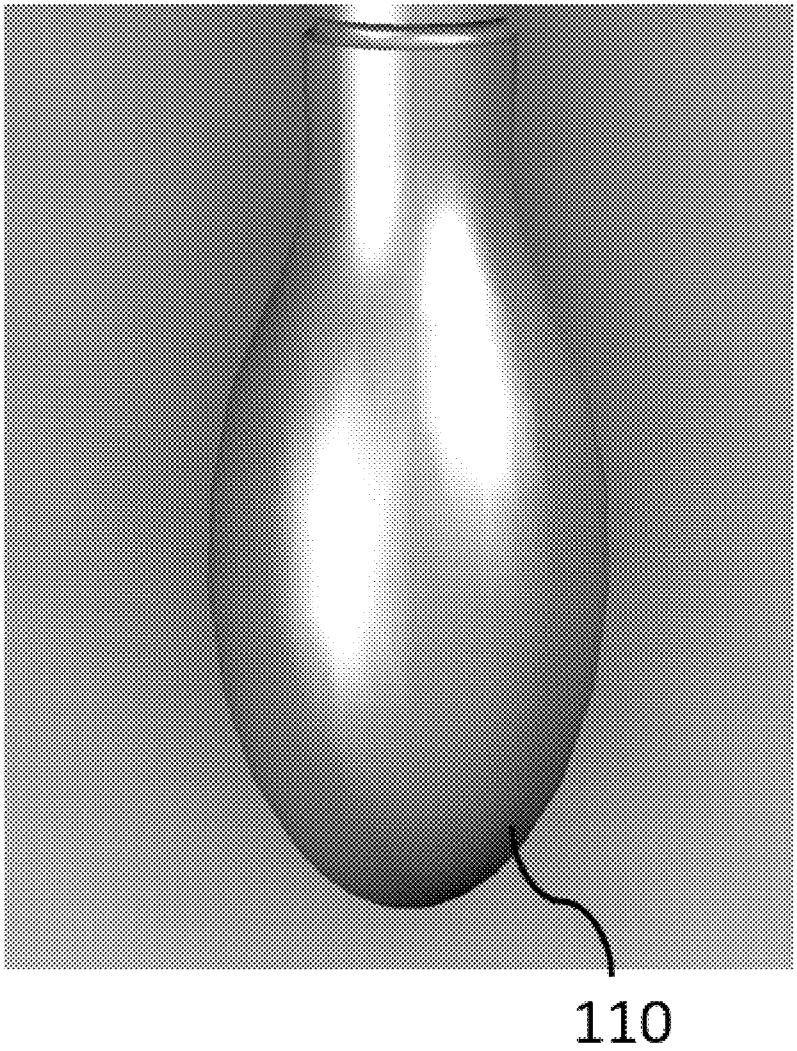
FIG. 14 shows the suction bulb. When the bulb is squeezed, it induces a suction at the receptacle.
Figure 15:
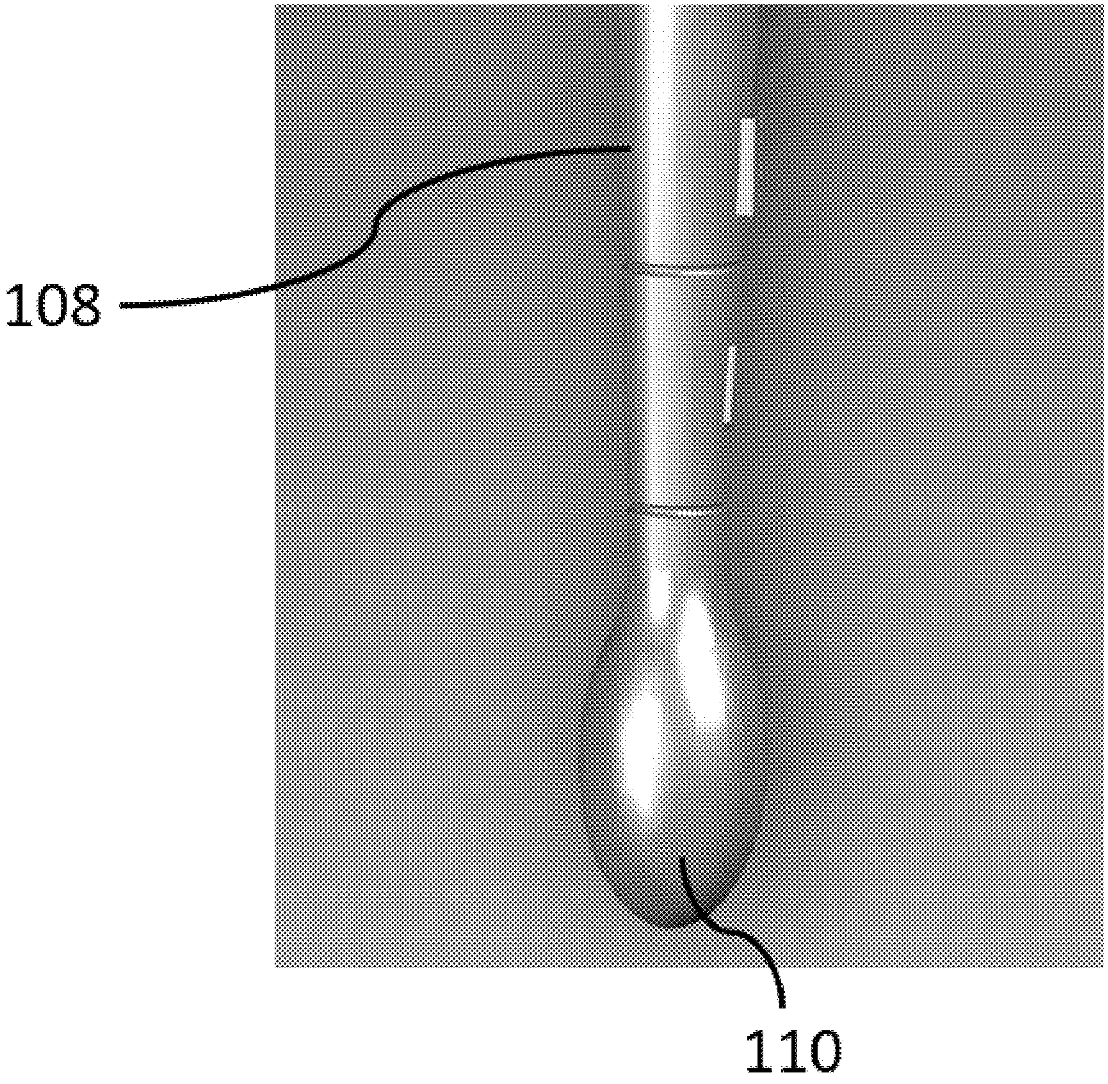
FIG. 15 shows the connection between the suction bulb and the drainage system. Because both the drainage and the suction mechanisms work in tandem with the hollow stem, when the drainage slot is open, the suction pressure is released, allowing for the suction to be intermittent.

The menstrual cup 100 generally terminates at the end of the stem 108 with a drainage means. The drainage means may be any selectably openable means to drain the fluid, such as a valve or a sealable orifice. The stem 108 may further comprise a means for applying a negative pressure to the interior of the stem and receptacle. In some embodiments, the means for applying a negative pressure is a suction bulb 110. In some embodiments, the means for applying a negative pressure is a suction bulb 110 which is permanently affixed to or formed as a portion of the telescoping stem 108 (see further, FIGS. 14 and 15). In some embodiments, the means for applying a negative pressure is a suction bulb 110 which is removably attached to the telescoping stem 108. Further views of the embodiment depicted in FIG. 1 are depicted in FIGS. 2 and 3. FIGS. 4 and 5 depict a receptacle with no telescoping stem attached, for illustrative purposes showing an illustrative hole 103 in the receptacle providing fluid access to the telescoping stem.

Figure 6:
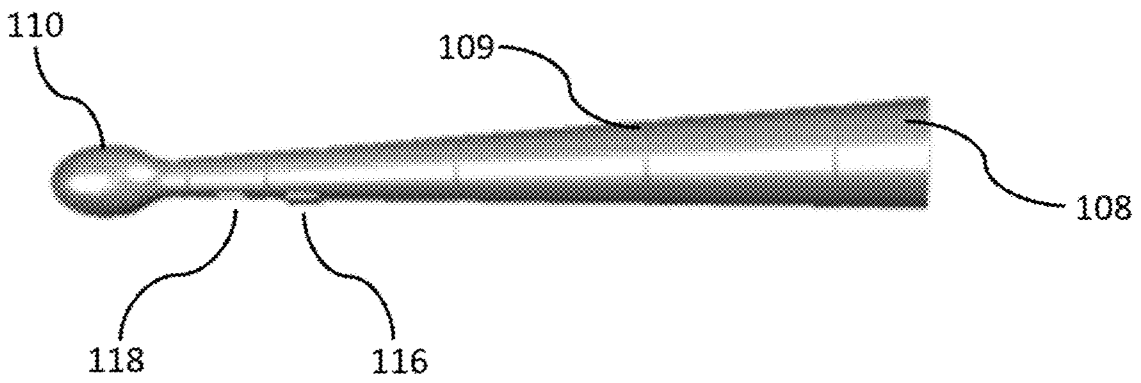
FIG. 6 shows a side view of the drainage system with the stem in its extended state and the location of the drainage slot as well as a tab that covers the slot when the drainage section is collapsed. The dashed arrow indicates the open drainage slot. The solid arrow indicates the drainage tab.
Figure 7:
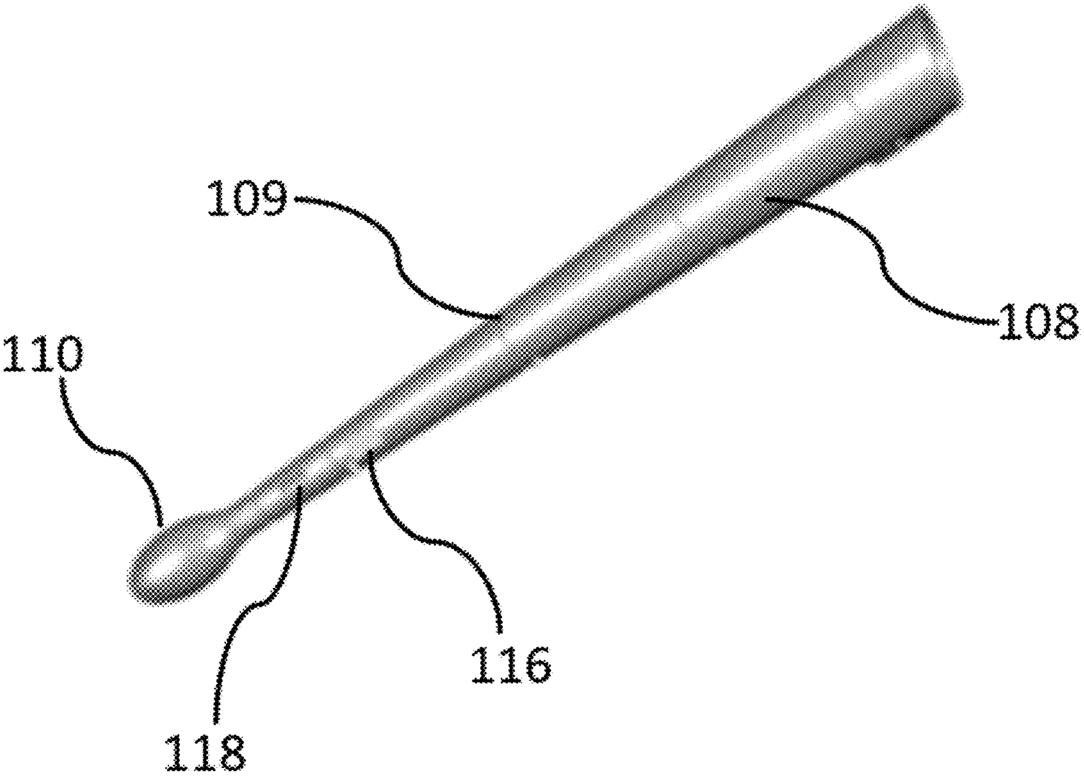
FIG. 7 shows a front view of the drainage system.
Figure 12A:
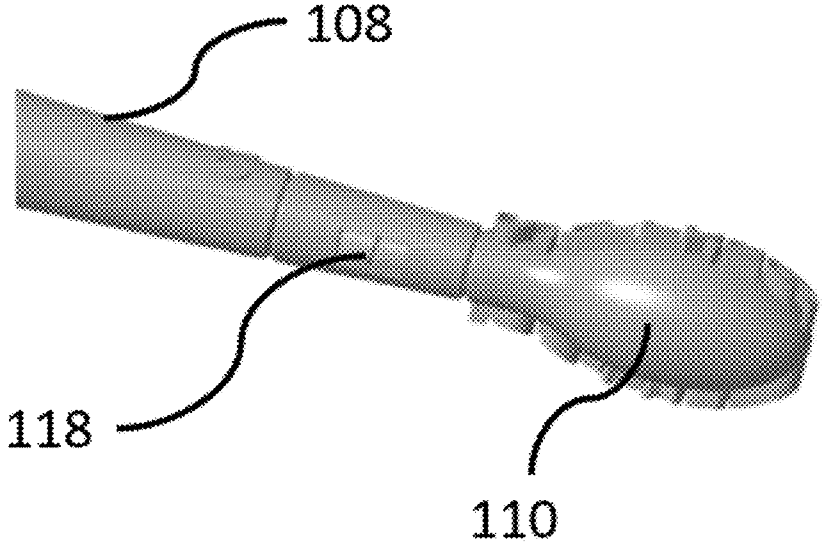
FIGS. 12A and 12B show the drainage feature of the stem of the menstrual cup.
Figure 12B:
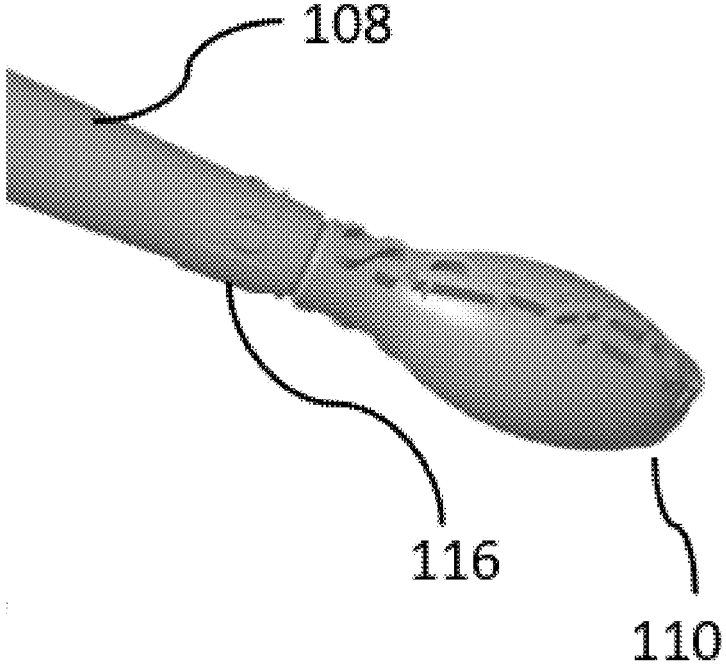

FIG. 6 depicts a hollow telescoping stem 108 having a drainage means. The depicted drainage means is a drainage slot 118 and a tab 116 which can be used to selectively open and close the drainage slot 118 (see further, FIG. 12). The drainage slot 118 may be used in conjunction with the suction bulb 110 to apply a negative pressure to the interior of the menstrual cup. FIG. 7 shows a further view of the embodiment depicted in FIG. 6.

Figure 8:
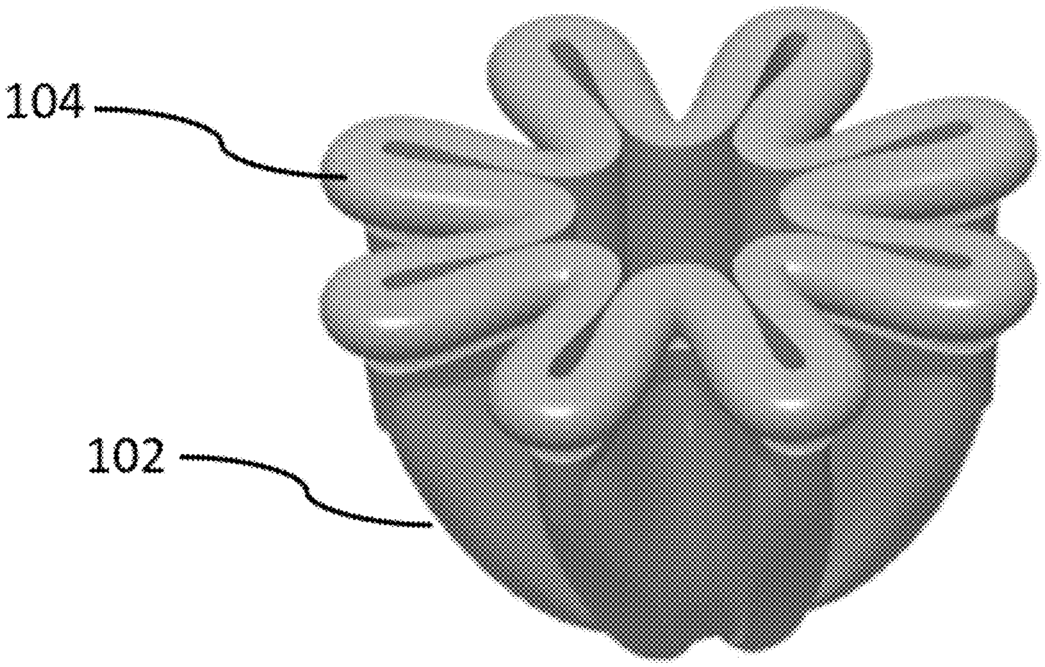
FIG. 8 shows the menstrual cup in its fully folded conformation.
Figure 9A:
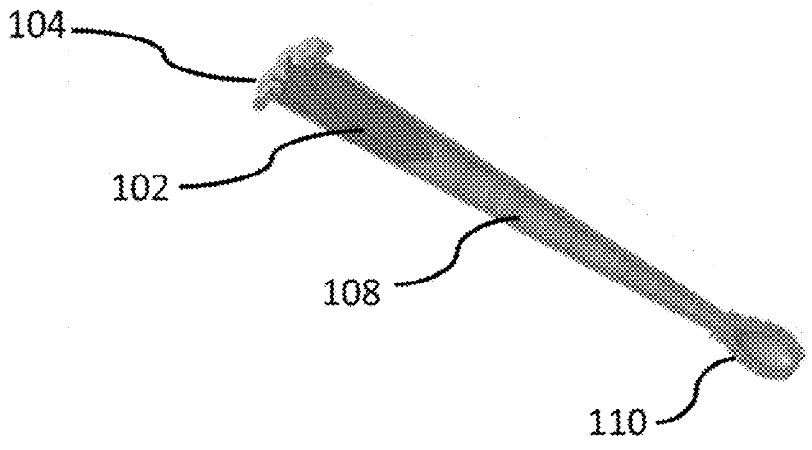
FIGS. 9A and 9B shows the orientation of the fully folded menstrual cup within the stem of the cup.
Figure 9B:
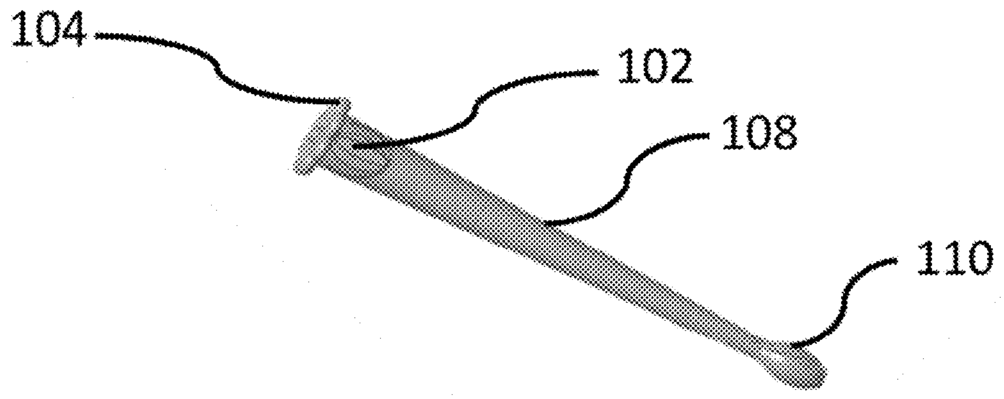
Figure 10:
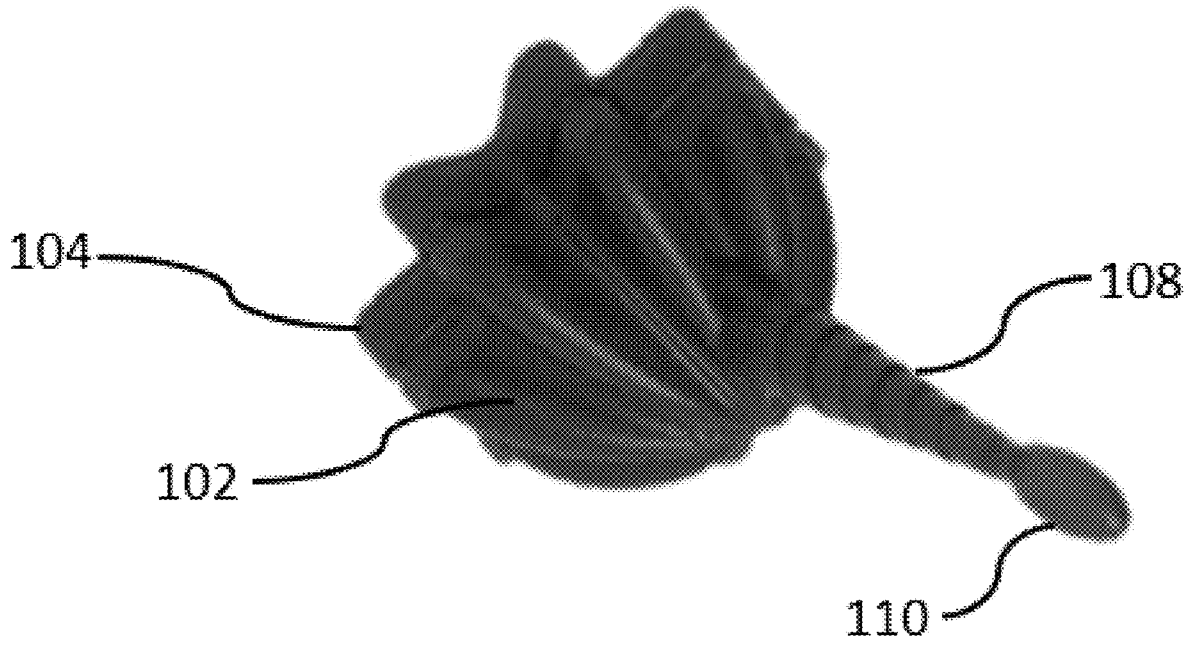
FIG. 10 shows the menstrual cup in a partially open position as the stem is partially collapsed.
Figure 11A:
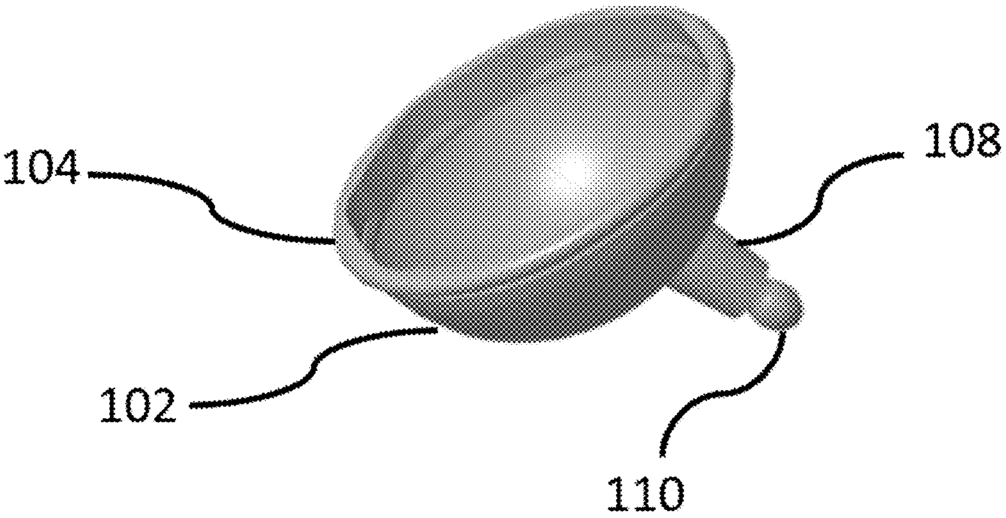
FIGS. 11A and 11B are two different perspective views showing the menstrual cup in the fully open and extended position with the stem fully collapsed.
Figure 11B:
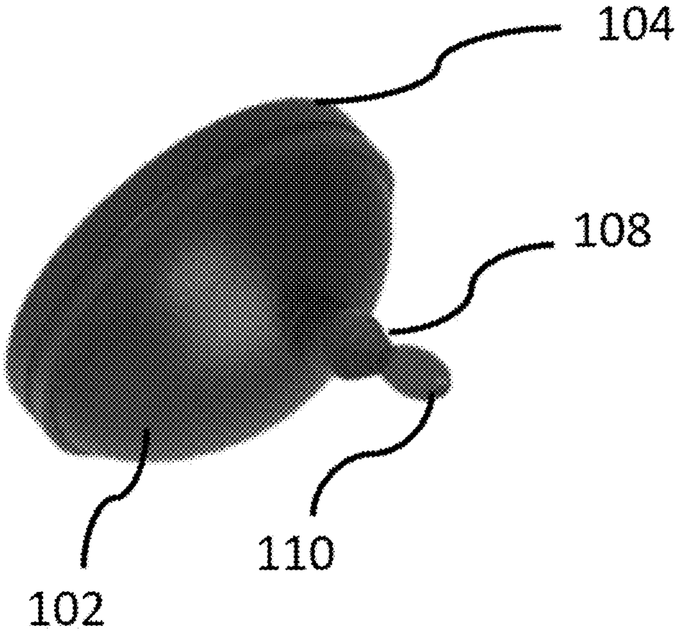
Figure 13A:
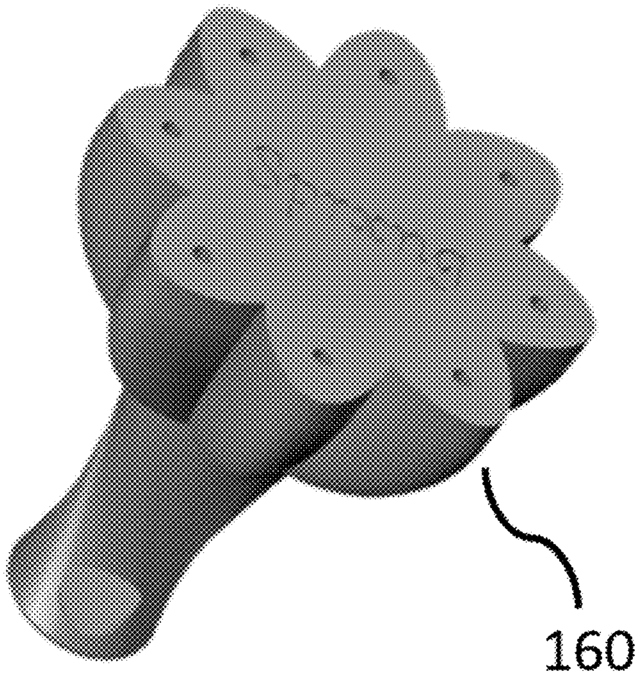
FIGS. 13A and 13B show two different perspective views of a carrying case for the menstrual cup.
Figure 13B:
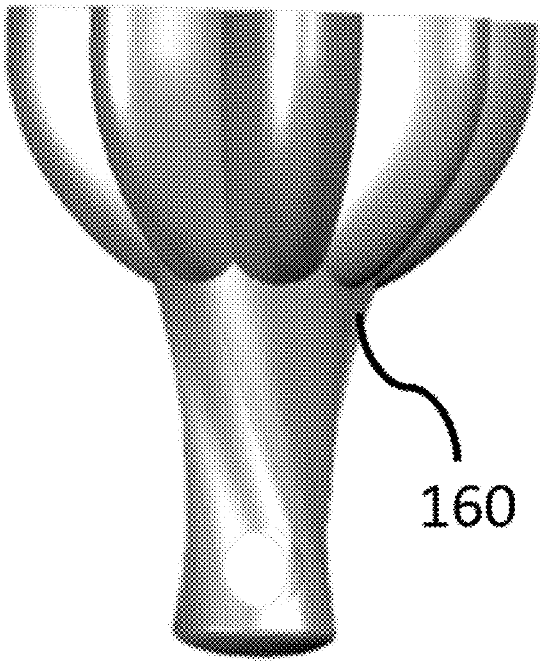
Figure 17:
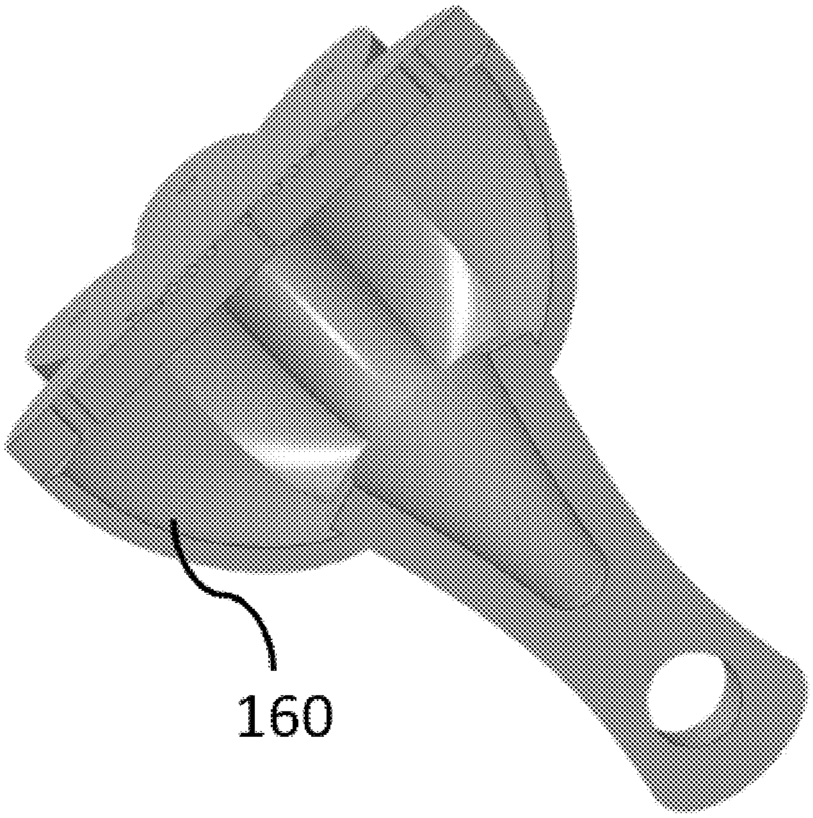
FIG. 17 shows a cross section of a carrying case. The case is designed for the user to collapse the device into the case to ensure that the device is in an ideal position when the user removes it from the case. The case fits the menstrual cup in its rest/starting shape.

FIG. 8 shows an exemplary embodiment of a receptacle in a folded state. The rim 104 is folded along its creases resulting in an overall flower-like profile with the creased regions projecting outwardly from a center aperture. The flower-like profile continues along the body of the receptacle to reduce the overall size of the receptacle along the circumferential direction or plane of the rim 104. The size of the receptacle is reduced to such an extent that the bottom portion of the receptacle, in its folded state, may be accepted by the adjacent portion of the telescoping stem 108, as depicted in FIG. 9. When inserted into the telescoping stem 108, the rim 104 of the receptacle 102 may protrude from the telescoping stem. A partially-unfolded state is shown in FIG. 10. FIG. 11 depicts an embodiment in an inserted state, with the receptacle expanded and the hollow telescoping stem fully retracted. FIGS. 13 and 17 depict an embodiment of a case for accepting the menstrual cup in a partially-folded state.

Figure 16:
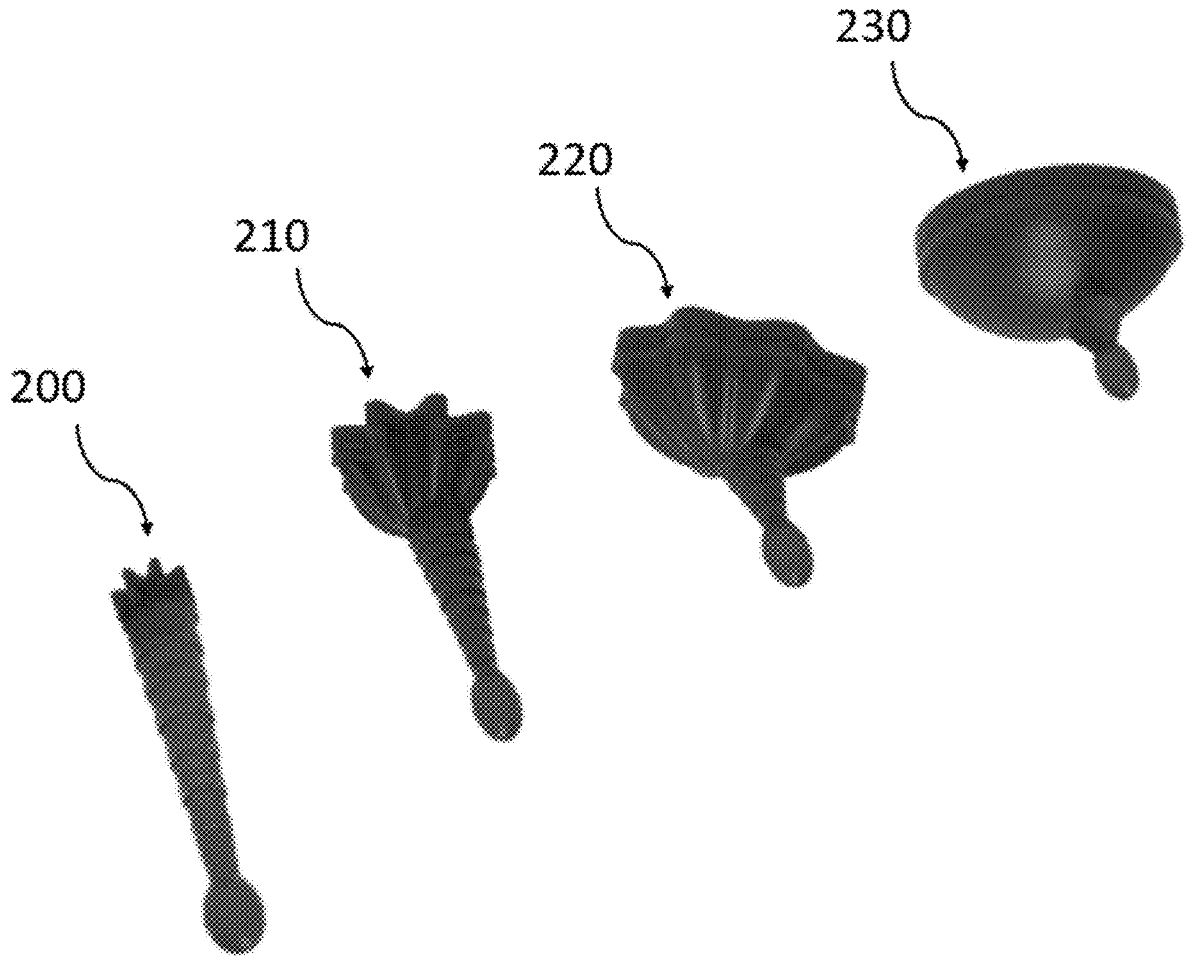
FIG. 16 shows the menstrual cup at different stages during insertion and demonstrates how the stem acts as a built-in applicator. The figure shows the receptacle completely closed, and as the stem is collapsed, the receptacle starts to open.

FIG. 16 depicts an exemplary embodiment in four states during the insertion process. As described herein, the receptacle is folded to fit partially within the adjacent portion of the telescoping stem, position 200. With the receptacle inserted into the vagina, the telescoping stem is retracted to expel the receptacle from the telescoping stem (positions 210 and 200) until the receptacle is fully expanded with the telescoping stem in a fully retracted position (position 230). Once the receptacle has captured fluid needing to be drained, the stem may be expanded for the user to access the drainage means and drain the fluid. The telescope may then be retracted again to position 230.

Figure 18:
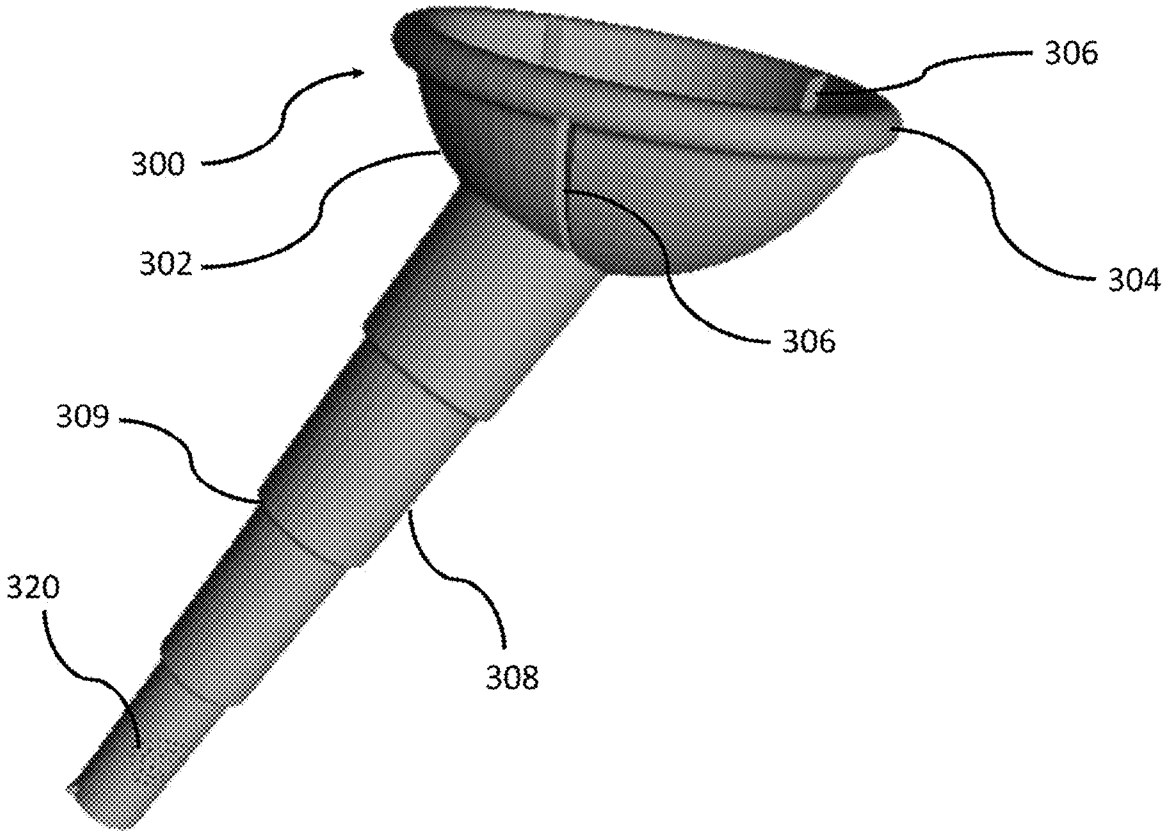
FIG. 18 depicts an exemplary embodiment having a telescoping stem with the telescoping stem in an extended state.

FIG. 18 depicts an exemplary embodiment of a menstrual cup 300 having a receptacle portion 302 with a rim 304 at its top and a hollow telescoping stem 308 disposed off-center on the base of the receptacle 302. The hollow telescoping stem 308 is in fluid communication with the receptacle 302. The rim 304 and/or receptacle have one or more creases 306 which may be located on the rim only, from the rim extending toward the base, or only below the rim. As shown in the exemplary embodiment, the creases 306 may be on the interior of the receptacle 302 or on the exterior of the receptacle 302. In the exemplary embodiment, the creases are located on both the interior and exterior of the receptacle 302 with the interior creases running from the rim 306 toward the base and the exterior creases being located only on the receptacle portion and not on the rim portion. It can be appreciated that any arrangement of the creases is contemplated.

The creases 306 each define a folding plane of the receptacle 302 such that the domed portion of the receptacle folds along the plane of the crease 306. The folding planes may generally be defined as orthogonal to the circumferential plane of the rim 304. The folding planes being orthogonal to the circumferential plane of the rim is particularly advantageous because the receptacle, when folded, will have a smaller circumference than the receptacle in its unfolded state (see, eg., FIGS. 8 and 16). This smaller circumferential profile is advantageous because insertion into the vagina and placement is easier and the unfolded circumference can be further dimensioned for secure placement and fluid retention once the receptacle is expanded.

The receptacle 302 is in fluid communication with the hollow telescoping stem 308. The hollow telescoping stem 308 is collapsible along one or more ribs 309 which are approximately parallel to the plane of the rim 304. In embodiments where the stem 308 is off-centered on the receptacle 302 it can be appreciated that the degree to which the ribs 309 are parallel with the rim 304 depends upon the profile of the receptacle and it is generally contemplated that the stem 308 telescopes toward or away from the receptacle 302. Generally, the stem 308 telescopes in a direction orthogonal to the folding planes of the receptacle 302. The orthogonality between the folding plane of the receptacle 302 and the telescoping direction of the stem 308 is particularly advantageous for the "origami style" folding capability of the devices as disclosed herein.

Figure 19:
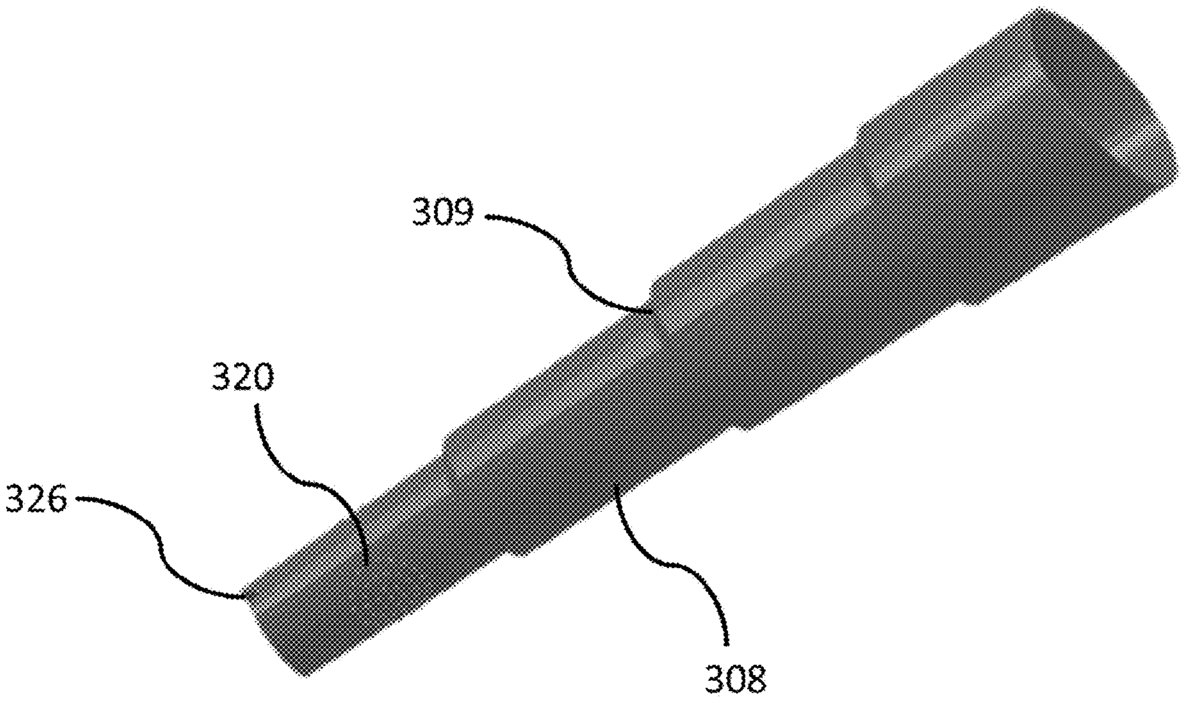
FIG. 19 depicts an exemplary telescoping stem terminating in an extended state.

The base of the hollow telescoping stem may have one or more tactile features 320 which assist the user in grasping the stem and also may allow the user to locate positions on the stem for actuating a valve in certain embodiments, as described herein. FIG. 19 shows a hollow telescoping stem including a protrusion 326 at a base of the hollow telescoping stem for engagement with one or more of a suction bulb or valve inserted into the base of the hollow telescoping stem. The protrusion 326 may be complementary to one or more features on a suction bulb or valve and may be useful for alignment, retainment, or both.

Figure 20A:
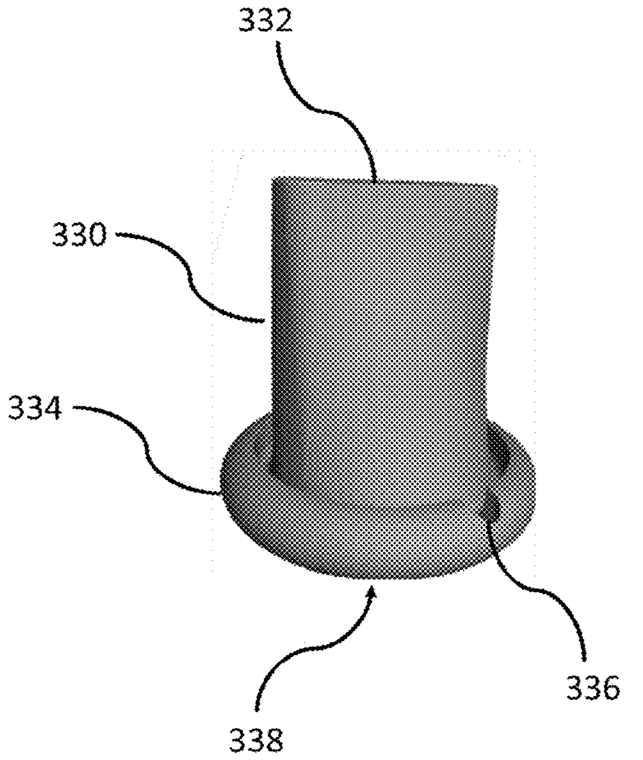
FIG. 20A depicts a front view of a duckbill valve.
Figure 20B:
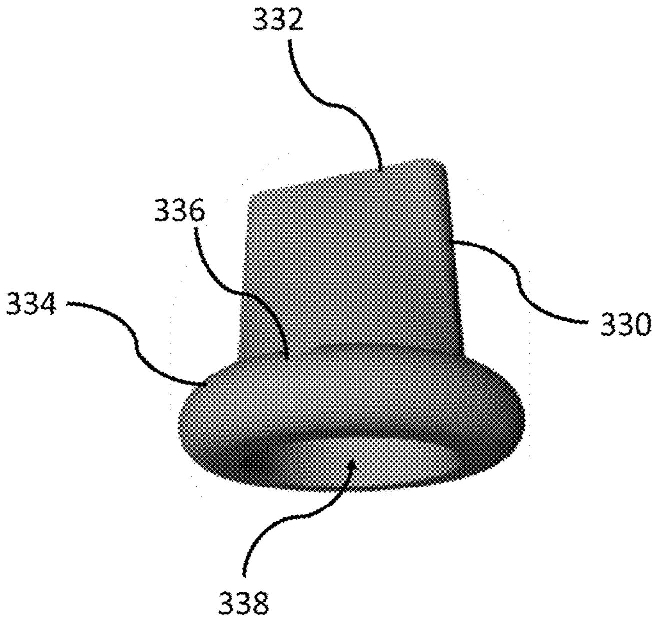
FIG. 20B depicts a perspective view of a duckbill valve.

FIGS. 20A and 20B show an exemplary embodiment of a valve for use with the menstrual cups and hollow telescoping stems of the present disclosure. The valve 330 may be a duckbill valve terminating in a slit 332 and opening at its base 338 defined by a rim 334. The rim 334 may have a notch for engagement with a protrusion 326 on the hollow telescoping stem. In an embodiment, the slit portion 332 is inserted inside of the base of the hollow telescoping stem such that the base of the hollow telescoping stem fits within the top of the rim 334 so that the rim 334 is a visible raised feature at the base of the hollow telescoping stem. The protrusion 326 of the stem and notch 336 of the valve may co-locate the valve with the tactile features 320 of the stem such that the user may pinch the stem at the tactile features 320 to open the valve. Likewise, the user may release the pinch to close the valve.

Figure 21:
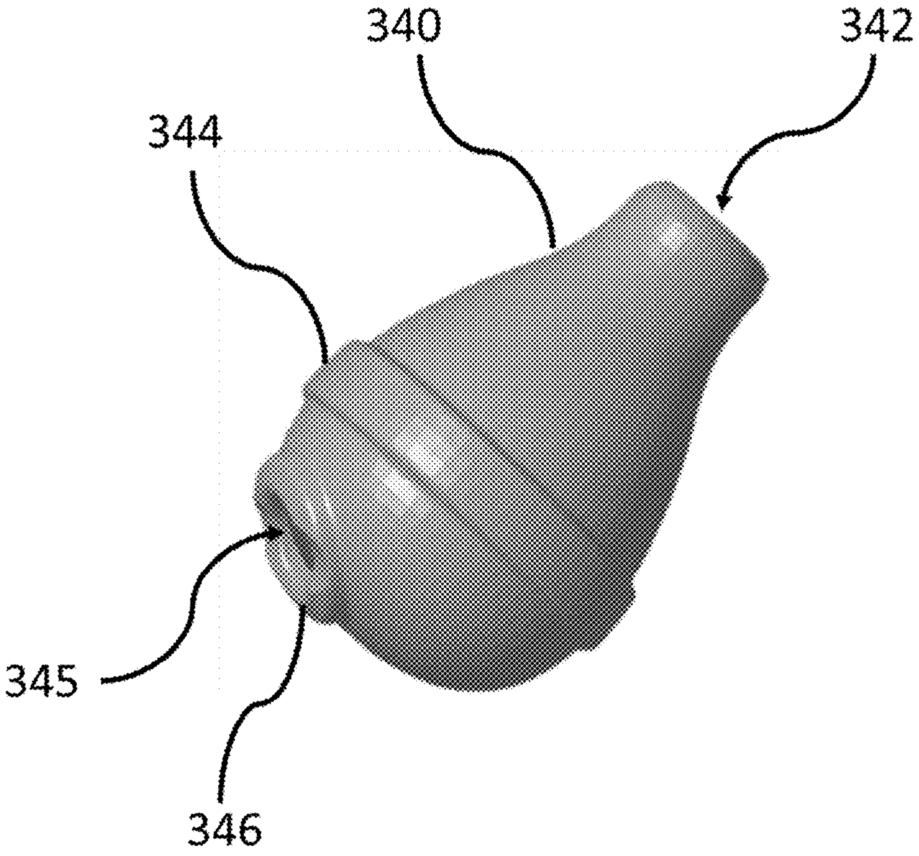
FIG. 21 depicts an exemplary bulb removably engageable with menstrual cups.
Figure 22A:
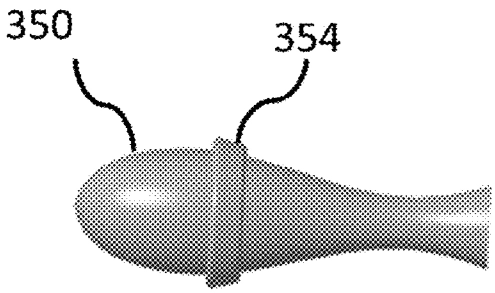
FIGS. 22A-22D depict an exemplary bulb removably engageable with menstrual cups.
Figure 22B:
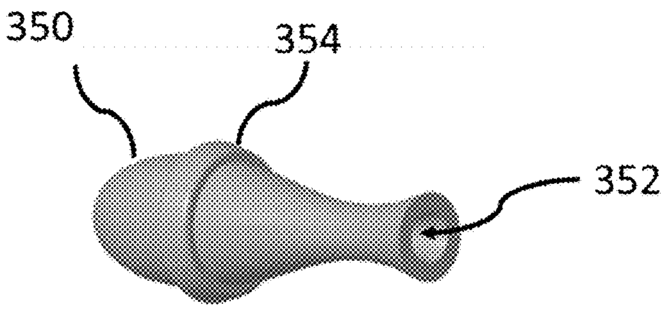
Figure 22C:
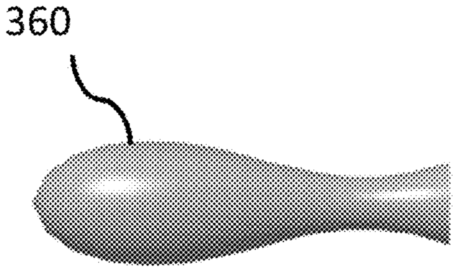
Figure 22D:
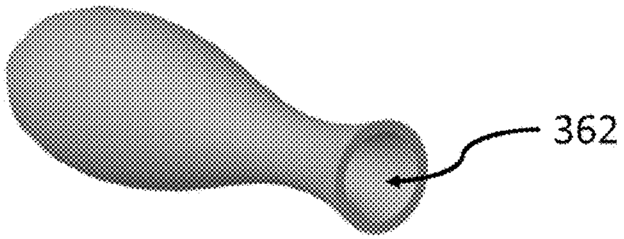

FIG. 21 depicts an exemplary embodiment of a suction bulb 340 having a first end 342 for engagement with a hollow telescoping stem or valve engaged therewith. The suction bulb may have one or more tactile features 346 for aligning the users grasp of the bulb. The bulb may also have one or more optional holes 345 for drainage or for selectively releasing the applied suction or negative pressure. The bulb may have one or more bands 344 which increase the elasticity of the bulb (i.e. the propensity for the bulb to return to its normal shape whilst having an applied negative pressure at its interior). In general, increasing the elasticity of the bulb will result in the user being able to apply more negative pressure before the bulb remains collapsed. Various bulb designs are contemplated including those shown in FIGS. 22A-D, which have a lengthened profile for enhanced comfort in the vaginal canal and which may therefore be comfortably left in place for a period of time to apply prolonged negative pressure. Bulb 350 has a band 354 and a relatively thick sidewall while bulb 360 does not have a band and has a relatively thin sidewall. Any combination of these various bulb features, including various bulb volumes, are contemplated.

Figure 23A:
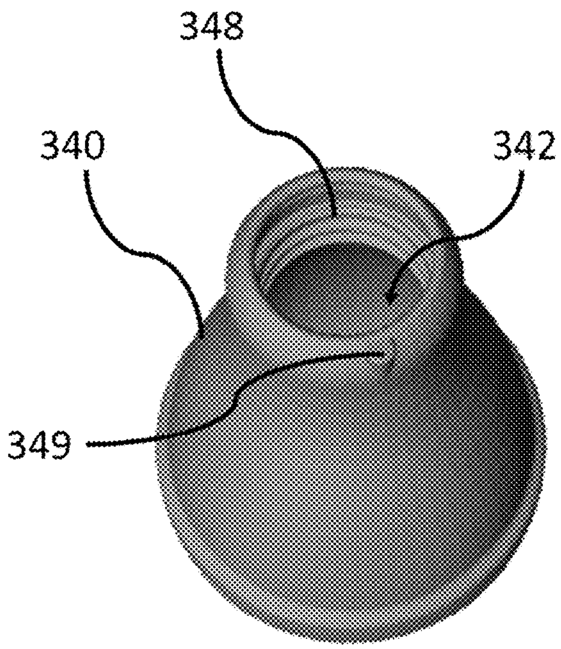
FIG. 23A depicts an exemplary bulb removably engageable with menstrual cups.
Figure 23B:
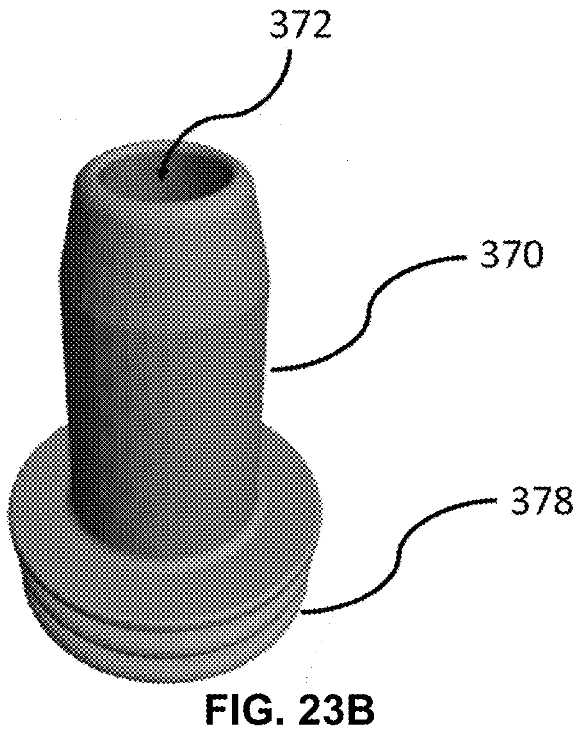
FIG. 23B depicts an exemplary straw removably engageable with bulbs.

FIGS. 23A-23B show a bulb and straw embodiment. In some embodiments, the user may insert a straw 370 through the valve to allow air and/or collected fluid to flow through the central channel 372 of the straw. The straw 370 may engage with the bulb 340 with ridged features 378 that retain the bulb on the stem and provide an airtight seal. The bulb may have a feature 349 for engagement with the protrusion 326 of the hollow telescoping stem.

Figure 24:
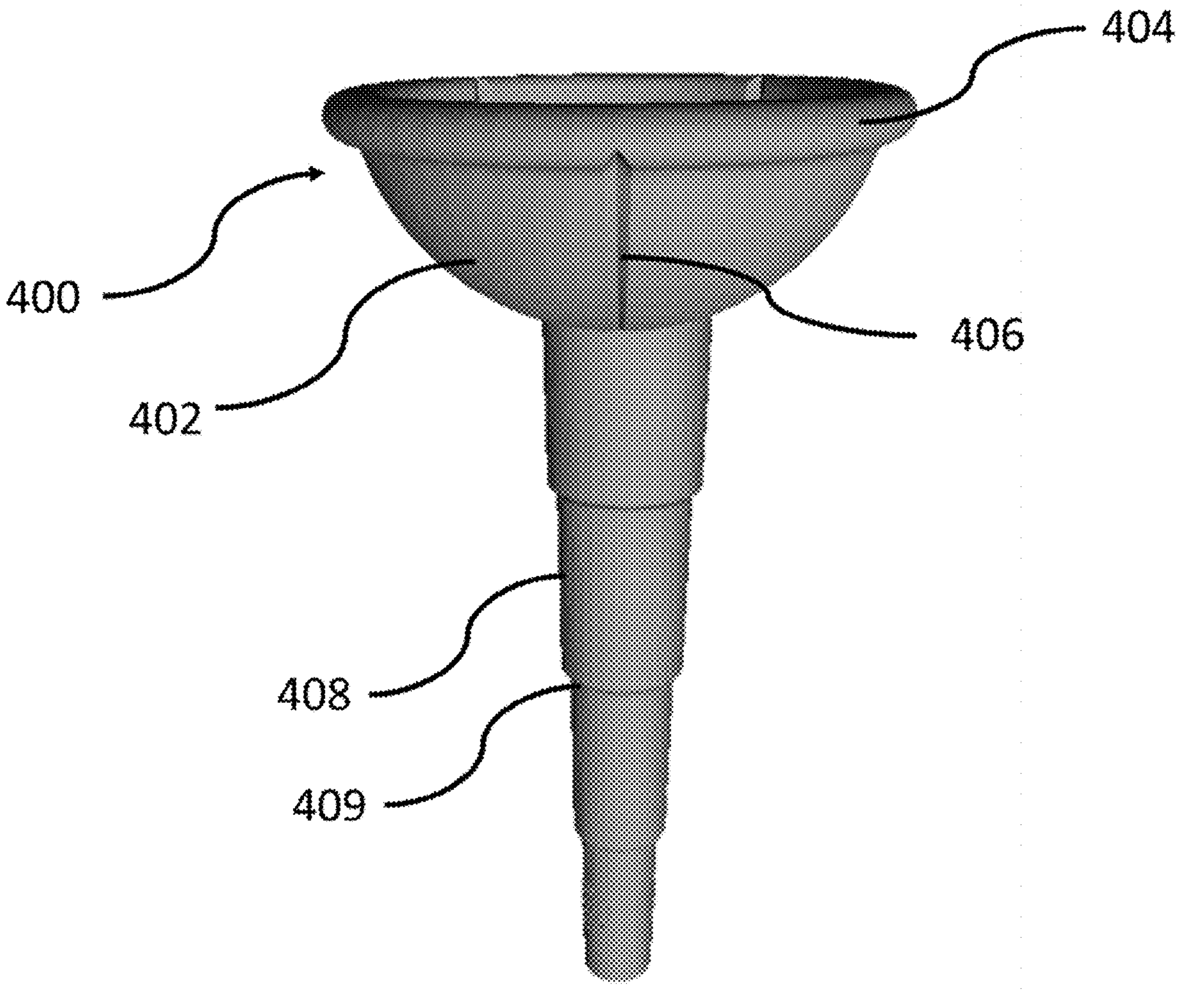
FIG. 24 depicts an exemplary menstrual cup having a hollow telescoping stem centered at its receptacle bottom.

FIG. 24 depicts an exemplary embodiment of a menstrual cup 400 having a receptacle portion 402 with a rim 404 at its top and a hollow telescoping stem 408 disposed and centered on the base of the receptacle 402. The hollow telescoping stem 408 is in fluid communication with the receptacle 402. The rim 404 and/or receptacle have one or more creases 406 which may be located on the rim only, from the rim extending toward the base, or only below the rim. As shown in the exemplary embodiment, the creases 406 may be on the interior of the receptacle 402 or on the exterior of the receptacle 402. In the exemplary embodiment, the creases are located on both the interior and exterior of the receptacle 402 with the interior creases running from the rim 406 toward the base and the exterior creases being located only on the receptacle portion and not on the rim portion. It can be appreciated that any arrangement of the creases is contemplated.

The creases 406 each define a folding plane of the receptacle 402 such that the domed portion of the receptacle folds along the plane of the crease 406. The folding planes may generally be defined as orthogonal to the circumferential plane of the rim 404. The folding planes being orthogonal to the circumferential plane of the rim is particularly advantageous because the receptacle, when folded, will have a smaller circumference than the receptacle in its unfolded state (see, eg., FIGS. 8 and 16). This smaller circumferential profile is advantageous because insertion into the vagina and placement is easier and the unfolded circumference can be further dimensioned for secure placement and fluid retention once the receptacle is expanded.

The receptacle 402 is in fluid communication with the hollow telescoping stem 408. The hollow telescoping stem 408 is collapsible along one or more ribs 409 which are approximately parallel to the plane of the rim 404. In embodiments where the stem 408 is off-centered on the receptacle 402 it can be appreciated that the degree to which the ribs 409 are parallel with the rim 404 depends upon the profile of the receptacle and it is generally contemplated that the stem 408 telescopes toward or away from the receptacle 402. Generally, the stem 408 telescopes in a direction orthogonal to the folding planes of the receptacle 402. The orthogonality between the folding plane of the receptacle 402 and the telescoping direction of the stem 408 is particularly advantageous for the "origami style" folding capability of the devices as disclosed herein.

Figure 25A:
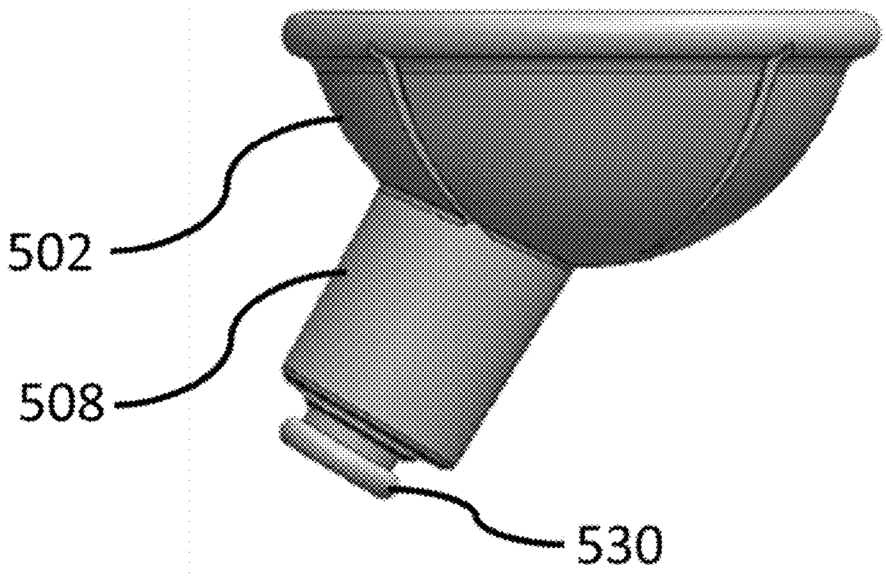
FIG. 25A shows an embodiment having a telescoping stem terminating in a valve with the telescoping stem in a compressed state.
Figure 25B:
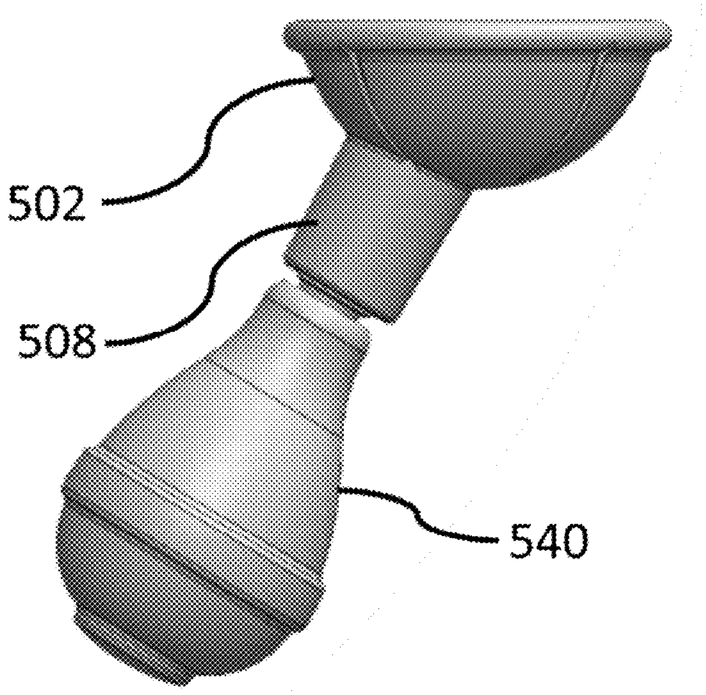
FIG. 25B shows an embodiment having a telescoping stem terminating in a valve with the telescoping stem in a compressed state and having an optional suction bulb coupled with the valve.

FIGS. 25A-25B show the attachment of the bulb to the menstrual cup in an embodiment. The bulb 540 engaged with the rim 530 of the valve and applies a circumferential pressure thereto for retainment and optionally to place the valve in a partially-opened state. Optionally, the bulb may attach to a straw inserted through the valve. Using the bulb 540, a negative pressure may be applied to the hollow telescoping stem 508 and the receptacle 502.

Figure 26A:
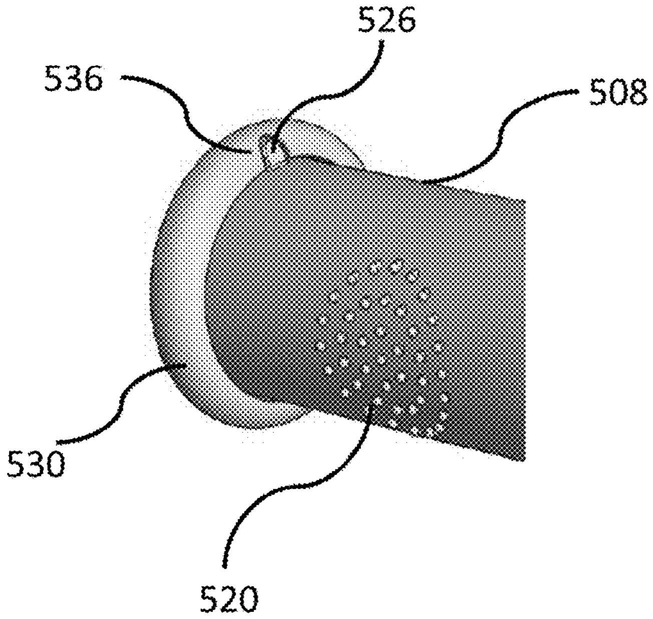
FIG. 26A shows an embodiment having tactile features located at a position on the telescoping stem relative to the valve orientation.
Figure 26B:
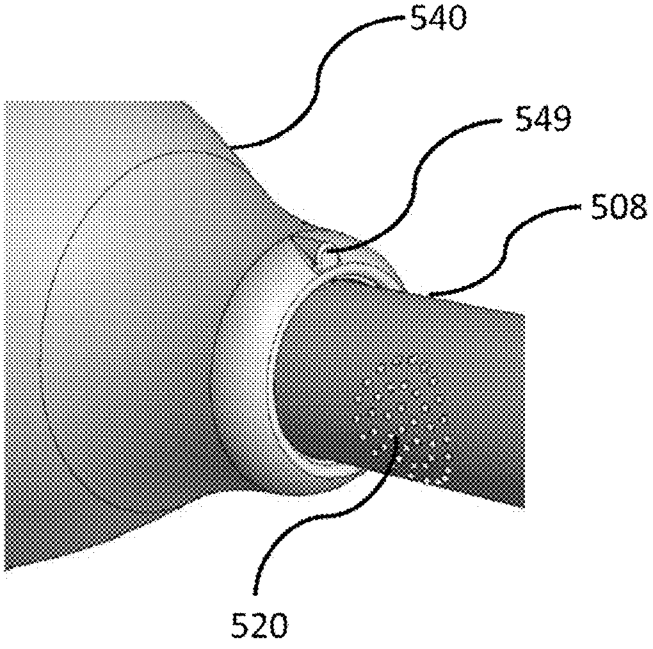
FIG. 26B shows an embodiment having tactile features located at a position on the telescoping stem relative to the valve orientation and having an optional suction bulb coupled with the valve.

FIGS. 26A-26B show a close-up view of the valve rim 530 aligned, using its notch 536, with the hollow telescoping stem 508 via its protrusion 526. The notch 536 is generally complementary to the protrusion 526 and any complementary features are contemplated. The bulb 540 may then be pressed over the valve rim 530 such that the alignment feature 549 of the bulb engages with the protrusion 526 of the stem. The alignment feature 549 of the bulb is optional and may not be present in some embodiments.

Figure 27A:
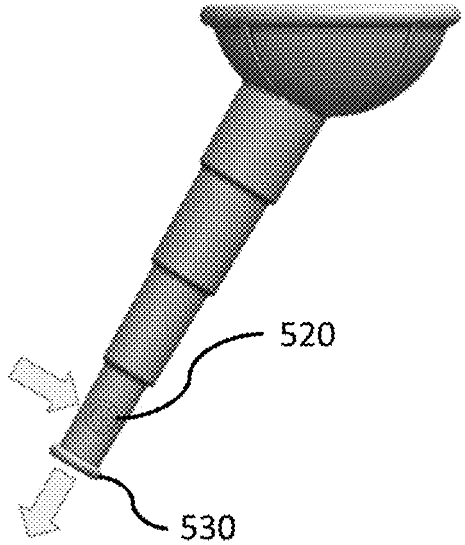
FIG. 27A shows an embodiment having a telescoping stem terminating in a valve with the telescoping stem in its fully extended state, with illustrative arrows indicating that pinching pressure applied to the valve via the telescoping stem exterior will open the valve to release the contents of the device.
Figure 27B:
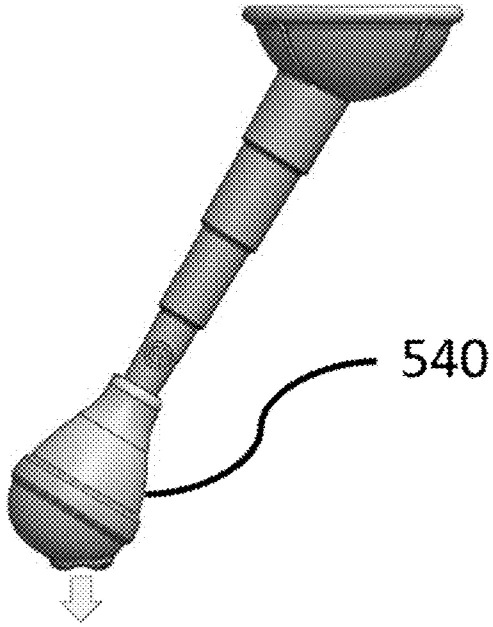
FIG. 27B shows an embodiment having a telescoping stem terminating in a valve with the telescoping stem in its fully extended state and having an optional suction bulb coupled with the valve, with an illustrative arrow showing where fluid may be released from a hole in the suction bulb.

FIGS. 27A-27B depict drainage of an exemplary embodiment with various drainage means. In some embodiments, the tactile features 520 may be squeezed to open the valve contained within the hollow telescoping stem. With the valve opened, fluid may drain from the stem and receptacle. In some embodiments, the user may attach a bulb 540 to the stem to apply a negative pressure. In the depicted embodiment, the bulb 540 has a drainage hole which may be selectively sealed by the user's finger to apply a negative pressure and/or to drain the contents of the menstrual cup.

Figure 28A:
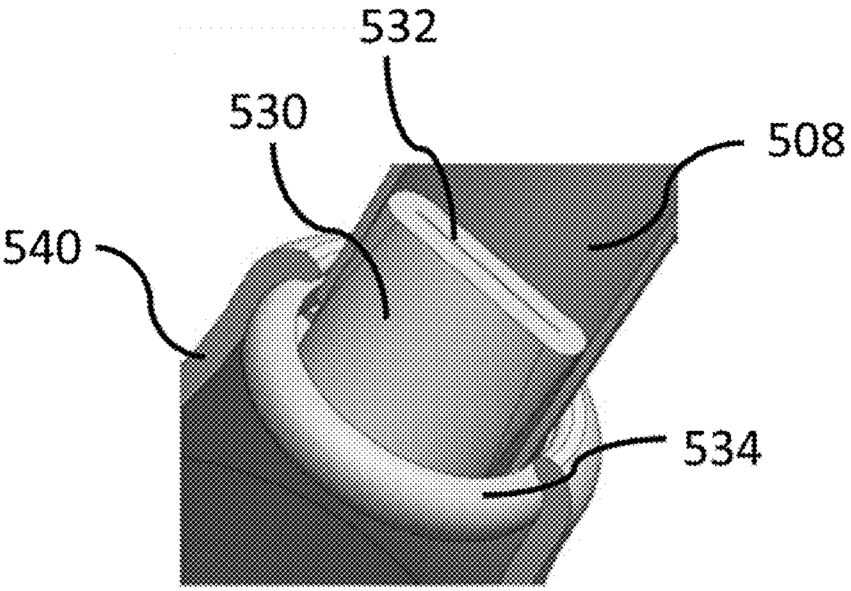
FIG. 28A shows a cross-section of the telescoping stem and bulb to expose a duckbill valve, with the arrows indicating the approximate positions at which an externally applied pressure will open the valve.
Figure 28B:
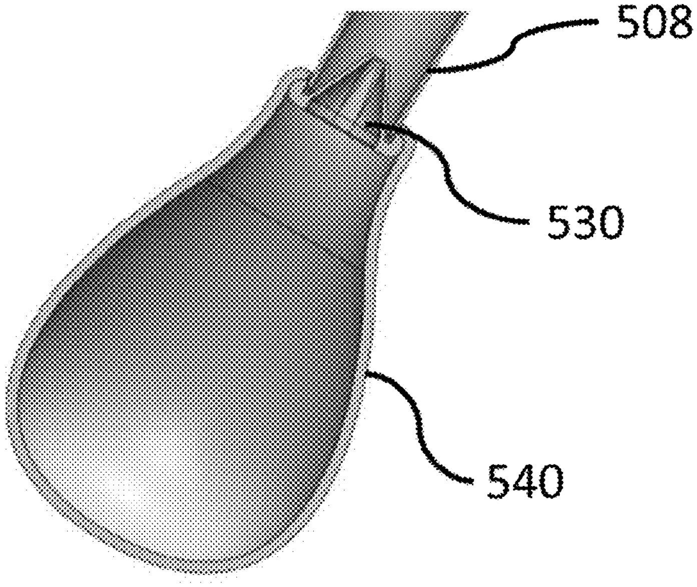
FIG. 28B shows a cross-section of the telescoping stem, bulb, and duckbill valve.

FIGS. 28A-28B depict cross-sectional views of the bulb 540 surrounding the hollow telescoping stem 508 and the rim 534 of the valve 530 inserted into the stem. The bulb 540 may apply a circumferential pressure or force to the rim 534 of the valve 530 sufficient to open the slit 532 of the valve for passage of air and/or fluid. In alternative embodiments, the user actuates the valve manually via the stem exterior. In further alternative embodiments, the bulb is attached to an inserted straw as described herein.

Carrying Case

The carrying case can have a variety of designs including a floral design with a hole near the bottom of the case. The purpose of the hole is to allow users to attach the case to objects as an accessory. The case is designed for the user to collapse the menstrual cup into its resting storage position.

Methods of Manufacture

The menstrual cup can be made out of silicone (including medical grade silicone) or latex rubber. The menstrual cup can be manufactured using a molding process. The molding process may be performed by injection molding or over molding. The mold tooling may comprise multiple components.

Use

During menstruation, the uterus contracts to help expel its endometrium lining. Menstrual blood flows from the uterus through the small opening in the cervix and passes out of the body through the vagina. In some women, the opening of the cervix is small enough to impede menstrual flow, causing a painful increase of pressure within the uterus.

Means for applying a negative pressure at the base of the stem may be used to create a negative pressure through the device. The suction facilitates menstrual blood flow and the expulsion of blood through the cervix. The means for applying may be a suction bulb, which may have finger alignment details for ergonomic use and/or for alignment with an optional vent hole.

Menstrual cramps can range from mild to severe. The expandable stem of the menstrual cup of the present invention allows for varying degrees of suction as the suction induced depends on the length of the stem at the time in which the bulb is compressed. In embodiments having releasably attachable and optional bulbs, the size of the bulb may also be changed to alter the amount of applied pressure. In some embodiments, the device is supplied with multiple bulbs having different volumes so as to allow the user to customize the applied negative atmospheric pressure. The suggested applied negative atmospheric pressure may also be determined by or prescribed by a medical professional, such as a physician.

The user generally inserts the device with the receptacle in its folded state, tucked into the stem, into the vagina and when the receptacle reaches the fornix, a user can collapse the stem to unfold and open the receptacle. Once the receptacle is in place in the vagina (vaginal fornix) the stem can be extended while the receptacle is still in place and completely open. By extending the telescoping stem the user will be able to actuate the drainage means or, optionally, apply negative pressure. This allows for the receptacle to be drained without it having to be removed from the vagina. The extended stem and receptacle in this position allow for the suction to be induced at the receptacle. The receptacle is removed by pulling the stem which in turn pulls out the receptacle. Alternatively, the receptacle can be removed by gripping the rim and pulling it out.

Users are encouraged to drain the device before removal. In the case that fluid is present in the receptacle during removal, the fluid is expected to flow into the stem when the stem is extended during removal, reducing the likelihood of spillage during removal.

Methods of Treatment

The devices of the present disclosure may be useful for methods of treatment of various conditional associated with the pelvic region or the female reproductive system. Generally, the devices are useful in methods of treatment for any conditions which may be prevented, treated, ameliorated, or improved by applying a negative pressure to the vagina, fornix, cervix, or any portion of the female reproductive system. In some embodiments, the negative pressure may alleviate pain or discomfort due to one or more conditions such as endometriosis, primary dysmenorrhea, secondary dysmenorrhea, and combinations thereof.

The present disclosure provides for methods of intrauterine cupping. "Intrauterine cupping" is the application a negative pressure (i.e. a negative atmospheric pressure, or suction) to the vagina, fornix, cervix, uterus, or any portion of the female reproductive system. The negative pressure may be intermittent (i.e. for a period of seconds or minutes), periodic (i.e. for a certain duration repeated a number of times, including rapid application and release of the negative atmospheric pressure) or sustained (i.e. for a period of many minutes-hours). The menstrual cups described herein may be used in methods of intrauterine cupping for any conditions which may be prevented, treated, ameliorated, or improved by applying a negative pressure to the vagina, fornix, cervix, uterus, or any portion of the female reproductive system.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the present invention, where the term comprises is used with respect to the recited components or methods, it is also contemplated that the invention consists essentially of, or consists of, the recited components or methods. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances an article of manufacture can be described as being composed of the components prior to assembly or incorporation into the article of manufacture.

All percentages and ratios used herein, unless otherwise indicated, are by weight. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

What is claimed is:

1. A collapsible menstrual cup, comprising:

a circular, concave receptacle having a rim comprising a plurality of creases disposed substantially orthogonal to a circumferential plane of the rim, the receptacle being collapsible and foldable along the creases into a folded state and conversely extendable and un-foldable into an unfolded state;

a hollow telescoping stem comprising an adjacent portion proximate to and in fluid communication with the concave receptacle and one or more distal portions nested concentrically within the proximal portion, the portions being telescopically movable between collapsed and extended configurations, wherein the receptacle in its folded state fits at least partially within the adjacent portion of the telescoping stem; and a discharge valve disposed at an end of the hollow telescoping stem distal to the concave receptacle.

2. The menstrual cup of claim 1 wherein the receptacle has a concave inner surface and a convex outer surface.

3. The menstrual cup of claim 1 wherein the discharge valve forms a portion of or is in fluid communication with a discharge orifice.

4. The menstrual cup of claim 1 wherein the discharge valve is a duckbill valve.

5. The menstrual cup of claim 4 wherein the discharge valve is contained at least partially within the distal end of the hollow telescoping stem.

6. The menstrual cup of claim 5 wherein a portion of the hollow telescoping stem surrounding the discharge valve comprises tactile features aligned with an actuation direction of the discharge valve.

7. The menstrual cup of claim 5 wherein the discharge valve comprises a rim protruding from and surrounding the distal end of the hollow telescoping stem.

8. The menstrual cup of claim 6 further comprising a suction bulb operable to apply a negative atmospheric pressure.

9. The menstrual cup according to claim 1 wherein the stem is offset from a center position of the receptacle.

10. The menstrual cup of claim 1 wherein the stem is located at a center position of the receptacle.

11. A method for collecting and/or draining menstrual fluid from a female subject, the method comprising the steps of:

collecting menstrual fluid in the receptacle of the menstrual cup of claim 1;

extending the telescoping stem; and discharging the collected menstrual fluid via the discharge valve of the telescoping stem.

12. A method of alleviating or reducing pressure on the vagina and/or the uterus in a female subject, the method comprising the steps of squeezing and releasing the suction bulb of the menstrual cup of claim 8 to create a negative atmospheric pressure at the vagina and/or the uterus of the female subject.

13. A method of relieving menstrual pain or discomfort in a female subject, the method comprising the steps of squeezing and releasing the suction bulb of the menstrual cup of claim 8 to facilitate removal of menstrual fluid and to relieve pressure on the vagina and/or the uterus.

* * * * *